United States Patent
Brown et al.

(10) Patent No.: US 6,600,052 B1
(45) Date of Patent: Jul. 29, 2003

(54) REGIOSELECTIVE SYNTHESIS OF 3,4-DI (CARBOCYCLYL OR HETEROCYCLYL) THIOPHENES

(75) Inventors: David L. Brown, Chesterfield, MO (US); Cindy L. Ludwig, St. Louis, MO (US)

(73) Assignee: Pharmacia Corporation, Skokie, IL (US)

( * ) Notice: Subject to any disclaimer, the term of this patent is extended or adjusted under 35 U.S.C. 154(b) by 20 days.

(21) Appl. No.: 09/838,986

(22) Filed: Apr. 20, 2001

Related U.S. Application Data

(60) Provisional application No. 60/199,533, filed on Apr. 25, 2000, and provisional application No. 60/253,380, filed on Nov. 27, 2000.

(51) Int. Cl.[7] .......................................... C07D 333/10
(52) U.S. Cl. ...................................................... 549/72
(58) Field of Search ........................................ 549/72

(56) References Cited

U.S. PATENT DOCUMENTS

| | | |
|---|---|---|
| 4,820,827 A | 4/1989 | Haber |
| 5,521,213 A | 5/1996 | Prasit et al. |
| 5,536,752 A | 7/1996 | Ducharme et al. |
| 5,550,142 A | 8/1996 | Ducharme et al. |
| 5,571,810 A | 11/1996 | Matsuo et al. |
| 5,698,584 A | 12/1997 | Black et al. |
| 5,981,576 A | 11/1999 | Belley et al. |

FOREIGN PATENT DOCUMENTS

| | | |
|---|---|---|
| WO | WO 91/19708 A1 | 12/1991 |
| WO | WO 94/15932 A1 | 7/1994 |
| WO | WO 95/00501 A1 | 1/1995 |

OTHER PUBLICATIONS

Allen et al., "A Revised Edition of Annual Volumes X–XIX". Org. Synth., 1943, pp. 156–158, Collective vol. 2.
Dembech et al., "Transformation of a–Assisted Carbanions into the Corresponding Trimethylsiloxy Derivatives using Bis(Trimethylsilyl)Peroxide." Tetrahedron, 1990, pp. 2999–3006, vol. 46, No., 8.
Dominguez et al., "A Convenient One–Pot Preparative Method for 4,5–Diarylisoxazoles Involving Amine Exchange Reactions." J. Org. Chem., 1996, pp 5435–5439, vol. 61.
Dominguez et al., "A Short and Efficient Synthesis of 4,5–Diarylpyrimidines." Synlett, 1995, pp. 955–956.
Nakayama et al., "General Synthesis of 2,5–Dihydrothiophenes (3–Thiolenes) From Diketo Sulfides." Tetrahedron Lett., 1985, pp. 1981–1982, vol. 26.
Gauthier et al., "Synthesis and Biological Evaluation of 2,3–Diarylthiophenes as Selective Cox–2 Inhibitors, Part II: Replacing the Heterocycle." Bioorg. Med. Chem. Lett., 1996, pp. 87–92, vol. 6.

Gupton et al., "The Application of Disubstituted Vinylogous Iminium Salts and Related Synthons to the Regiocontrolled Preparation of Unsymmetrical 2,3,4–Trisubstituted Pyrroles[1]." Tetrahedron, 1998, pp. 5075–5088, vol. 54.
Gans et al., "Anti–Inflammatory and Safety Profile of DuP 697, a Novel Orally Effective Prostaglandin Synthesis Inhibitor." Pharmacol. Exp. Ther., 1990, pp. 180–187, vol. 254.
Hinsberg, O., "Synthetische Versuche mit Thiodiglykosaureester." Ber, 1910, pp. 901–906, vol. 43.
Sanmartin et al., "A Convenient Alternative Route to β–Aminoketones." Tetrahedron, 1994, pp. 2255–2264, vol. 50.
Bertenshaw et al.,"3,4–Diarylthiophenes Are Selective Cox–2 Inhibitors." Bioorg. Med. Chem. Lett., 1995, pp. 2919–2922, vol. 5.
Kim et al., "A new synthetic protocol for the direct preparation of organomanganese reagents; organomanganese tosylates and mesylates." Tetrahedron Lett., 1999, pp. 4931–4934, vol. 40.
Weissenfels, Zur Kondensation von β–Chlorvinylcarbon Iverbin–duen mit a–MercaptocarbonsaurenZ. Chem, 1973, pp. 57–58, vol. 13.
Chadwick et al., Preparation of Thiophen Esters by the Hinsberg Reaction, J. Chem. Soc.,1972, pp. 2079–2081.
Hauptmann et al., Substituierte Thiophene and Pyrrole aus 2–Color–vinylketonen, Z. Chem., 1969, p. 22, vol. 9, No. 1.
Joseph et al., Tetracyclic compounds from tetrahydrocarbazolones. Part 1. Synthesis from 2,3,4, 9–tetrahydrocarbazol–1–ones, J. Chem. Res. Miniprint, 1995, pp. 2001–2020, vol. 9.

Primary Examiner—Alan L. Rotman
Assistant Examiner—Golam M. M. Shameem

(57) ABSTRACT

A novel process for preparing 3,4-di(carbocyclyl or heterocyclyl)thiophenes comprising reacting a compound of Formula IV:

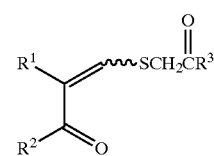

IV with a ring cyclizing reagent to form the compound of Formula V to yield a compound of Formula V:

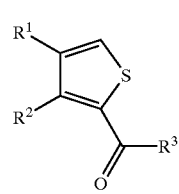

V wherein $R^1$, $R^2$ and $R^3$ are as defined in the specification.

23 Claims, No Drawings

REGIOSELECTIVE SYNTHESIS OF 3,4-DI(CARBOCYCLYL OR HETEROCYCLYL) THIOPHENES

This application claims benefit of 60/199,533 Apr. 25, 2000 and claims benefit of 60/253,380 Nov. 27, 2000.

FIELD OF THE INVENTION

This invention is in the field of processes for the preparation of thiophene compounds. The invention particularly relates to processes for the regioselective preparation of 3,4-di(carbocyclyl or heterocyclyl)thiophenes, particularly 3,4-di(aryl or heteroaryl)thiophenes.

BACKGROUND OF THE INVENTION

Selected 3,4-di(aryl or heteroaryl)thiophene compounds have been disclosed in the literature as inhibitors of the cyclooxygenase-II enzyme. K. R Gans et al., *Pharmacol. Exp. Ther.* 1990, 254, 180. These thiophene compounds are useful as antiinflammatory and analgesic pharmaceutical agents. See, for example, WO94/15932. Conventional processes for the preparation of such thiophenes generally are not regioselective and require separation of isomeric mixtures to obtain the desired thiophene. Accordingly, there has been increased interest in improved processes for the preparation of 3,4-di(aryl or heteroaryl)thiophene compounds and improved processes for the preparation of intermediate compounds used in the preparation of such 3,4-di(aryl or heteroaryl)thiophenes.

One conventional method of preparing 3,4-diarylthiophenes is through a Hinsberg synthesis by the condensation of dithioglycolate esters with arylsubstituted benzoins. O. Hinsberg, Ber. 1910, 43, 901. This method, however, is not regioselective. When a thiophene possessing a specific regiochemistry is desired, the desired thiophene typically is obtained through (a) unselective base saponification of a single ester, (b) separation of the resulting isomers to obtain the desired isomer, and (c) manipulation of the desired isomer to introduce the necessary functional group or groups. S. R. Bertenshaw et al., *Bioorg. Med. Chem. Lett.* 1995, 5, 2919–2922; and J. Nakayama et al., *Tetrahedron Lett.* 1985, 26, 1981. This approach is illustrated in Comparative Scheme A below:

COMPARATIVE SCHEME A

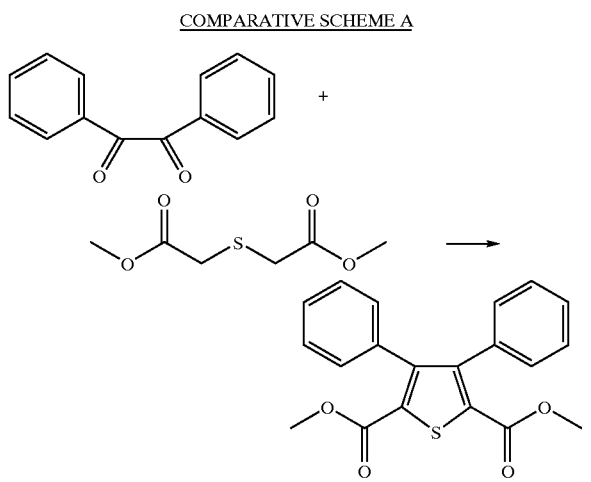

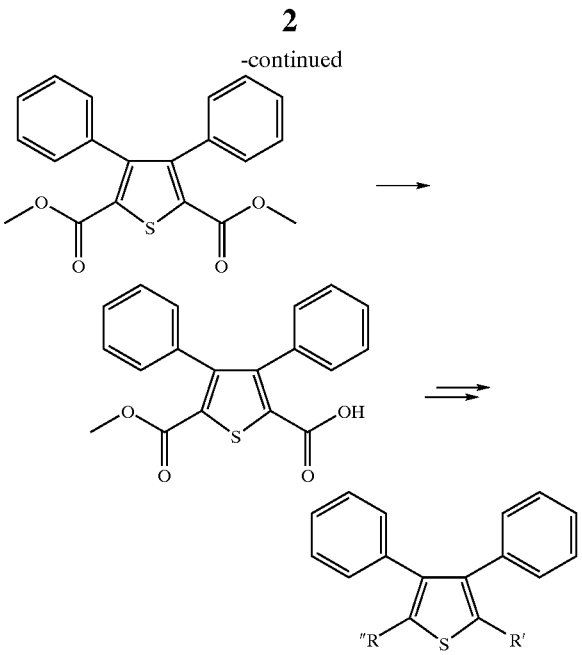

Another method for introducing a desired functional group to the thiophene ring requires electrophilic substitution of the thiophene. Regioselectivity of the resulting thiophene using the electrophilic substitution method can be achieved through introduction of differential electronic donating and withdrawing groups on the aromatic rings. This approach, however, is limited in scope and does not allow for the preparation of certain desirable substitutions of the thiophene ring. J. Y. Gauthier et. al., *Bioorg. Med. Chem. Lett.* 1996, 6, 87.

Scheme XIII of WO94/15932 discloses a non-regioselective method for the preparation of 3,4-diarylthiophenes wherein a thioacetylketone is coupled with a haloacetophenone to form a dione which is then converted to the thiophene in a modified McMurray synthesis.

WO95/00501 discloses a method for the preparation of 2,3-disubstituted thiophenes. In Method A of WO95/00501, a ketone is reacted with the Vilsmeier reagent (dimethylformamide-phosphorus oxychloride) to form a β-chlorovinylaldehyde. The β-chlorovinylaldehyde is then converted to a 2,3-disubstituted thiophene in accordance with the method of Weissenfels, Z. Chem., 1973, 13, 57. Regiochemistry of the thiophene can be controlled by selection of the desired ketone starting material. U.S. Pat. No. 4,820,827 discloses a similar conversion.

E. Dominguez et al., *Synlett,* 1995, 955–956, describes the preparation and use of a vinylogous amide as a starting compound for the synthesis of diarylpyrimidines.

R. Sanmartin et al., *Tetrahedron* 1994, 50, 2255–2264, describes the preparation and use of a vinylogous amide as a starting compound for the synthesis of β-aminoketones.

J. T. Gupton et al., *Tetrahedron* 1998, 54, 5075–5088, describes the preparation and use of a vinylogous amide as a starting compound for the synthesis of diarylpyrroles.

E. Dominguez et al., *J. Org. Chem.* 1996, 61, 5435–5439, describes the preparation and use of a vinylogous amide as a starting compound for the synthesis of diarylisoxazoles.

Accordingly, an improved process for the preparation of 3,4-di(carbocyclyl or heterocyclyl)thiophenes would be desirable, particularly a process that permits the regioselective preparation of a broad range of thiophenes and that is not dependent on the electronic nature of carbocyclyl or heterocyclyl rings attached to the thiophene ring.

SUMMARY OF THE INVENTION

The present invention is directed to an improved processes for the regioselective preparation of 3,4-di(carbocyclyl or heterocyclyl)thiophenes. In one aspect, the invention comprises a process for the preparation of a compound of Formula IV:

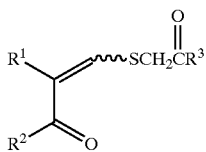

IV by reacting a compound of Formula III:

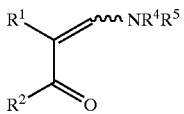

III with a compound selected from the group consisting of thioacetic acid, esters of thioacetic acid and amides of thioacetic acid to form the compound of Formula IV, wherein:

$R^1$ is selected from optionally substituted carbocyclyl and heterocyclyl;

$R^2$ is selected from optionally substituted carbocyclyl and heterocyclyl;

$R^3$ is selected from —$OR^6$ and —$NR^7R^8$;

$R^4$ and $R^5$ are independently selected from hydrogen and optionally substituted alkyl; and $R^6$, $R^7$ and $R^8$ are independently selected from hydrogen, hydrocarbyl and heterosubstituted hydrocarbyl.

In another aspect, the present invention comprises a process for the preparation of a compound of Formula V:

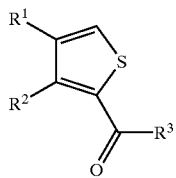

V by reacting a compound of Formula IV:

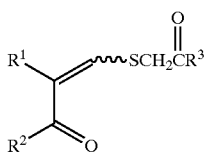

IV with a ring cyclizing reagent to form the compound of Formula V, wherein:

$R^1$ is selected from optionally substituted carbocyclyl and heterocyclyl;

$R^2$ is selected from optionally substituted carbocyclyl and heterocyclyl;

$R^3$ is selected from —$OR^6$ and —$NR^7R^8$; and $R^6$, $R^7$ and $R^8$ are independently selected from hydrogen, hydrocarbyl and heterosubstituted hydrocarbyl.

In another aspect, the present invention comprises a process for the regioselective preparation of 3,4-diphenylthiophenes comprising (a) reacting a deoxybenzoin with thioacetic acid or an ester or amide of thioacetic acid to form a Michael addition product, wherein (i) the deoxybenzoin comprises at least two double bonds conjugated with the same or different electron withdrawing groups, (ii) the dexoybenzoin comprises two phenyl moieties that are differently substituted, and (iii) the reaction is a nucleophilic addition reaction, and (b) cyclizing the Michael addition product to form a 3,4-diphenylthiophene.

In another aspect, the present invention comprises a process for the regioselective preparation of 3,4-diphenylthiophenes comprising (a) preparing a deoxybenzoin comprising (i) at least two double bonds conjugated with the same or different electron withdrawing groups and (ii) two phenyl moieties that are differently substituted, (b) reacting the deoxybenzoin with thioacetic acid or an ester or amide of thioacetic acid to form a Michael addition product, wherein the reaction is a nucleophilic addition reaction, and (c) cyclizing the Michael addition product to form a 3,4-diphenylthiophene.

In another aspect, the present invention comprises a process for the regioselective preparation of 3,4-diphenylthiophenes comprising (a) preparing a deoxybenzoin comprising two phenyl moieties that are differently substituted, (b) introducing a Michael acceptor into the primary carbon chain of the deoxybenzoin to provide a deoxybenzoin comprising at least two double bonds conjugated with the same or different electron withdrawing groups, (c) reacting the deoxybenzoin with thioacetic acid or an ester or amide of thioacetic acid to form a Michael addition product, wherein the reaction is a nucleophilic addition reaction, and (d) cyclizing the Michael addition product to form a 3,4-diphenylthiophene.

DESCRIPTION OF THE INVENTION

The present invention comprises processes for the regioselective preparation of 3,4-di(carbocyclyl or heterocyclyl) thiophenes, particularly processes that do not depend on the electronic nature of a carbocyclyl or heterocyclyl ring attached to the thiophene ring, as well as processes for the preparation of intermediate compounds useful in the the regioselective preparation of 3,4-di(carbocyclyl or heterocyclyl)thiophenes. The novel processes result in the formation of a thiophene ring wherein a single ester or amido functionality is selectively introduced to the ring at a position adjacent to the sulfur heteroatom while the other position of the ring adjacent to the sulfur heteroatom remains unsubstituted. Selection of the proper starting material for the cyclization reaction by which the thiophene is formed controls the regioselectivity of the resulting thiophene. The 3,4-di(carbocyclyl or heterocyclyl) thiophenes comprising the ester or amido functionality can then be used as a final product or can be further modified to yield other desirable thiophenes.

Preparation of Michael Addition Product

In accordance with a process of the present invention, a compound of Formula III:

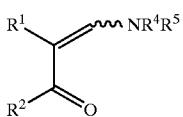

is reacted with a compound selected from the group consisting of thioacetic acid, esters of thioacetic acid and amides of thioacetic acid to form a compound of Formula IV:

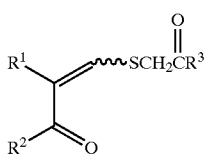

wherein:
$R^1$ is selected from optionally substituted carbocyclyl and heterocyclyl;
$R^2$ is selected from optionally substituted carbocyclyl and heterocyclyl;
$R^3$ is selected from —$OR^6$ and —$NR^7R^8$;
$R^4$ and $R^5$ are independently selected from hydrogen and optionally substituted alkyl; and
$R^6$, $R^7$ and $R^8$ are independently selected from hydrogen, hydrocarbyl and heterosubstituted hydrocarbyl.

The compound of Formula III preferably is reacted with $HSCH_2C(O)R^3$ to form the compound of Formula IV, wherein:
$R^1$ is selected from optionally substituted cycloalkyl, cycloalkenyl, aryl and heteroaryl;
$R^2$ is selected from optionally substituted cycloalkyl, cycloalkenyl, aryl and heteroaryl;
$R^3$ is selected from —$OR^6$ and —$NR^7R^8$;
$R^4$ and $R^5$ are independently selected from optionally substituted alkyl; and
$R^6$, $R^7$ and $R^8$ are independently selected from hydrogen and optionally substituted alkyl, alkenyl, alkynyl, cycloalkyl, cycloalkenyl, aryl, heterocyclyl, arylalkyl and heterocyclylalkyl, wherein said alkyl may have one or more carbon atoms that are optionally replaced with oxygen atoms.

In another embodiment, the compound of Formula III is reacted with $HSCH_2C(O)R^3$ to form the compound of Formula IV wherein:
$R^1$ is selected from optionally substituted aryl and 5- or 6-membered ring heteroaryl;
$R^2$ is selected from optionally substituted aryl and 5- or 6-membered ring heteroaryl;
$R^3$ is selected from —$OR^6$ and —$NR^7R^8$;
$R^4$ and $R^5$ are independently selected from optionally substituted alkyl; and
$R^6$, $R^7$ and $R^8$ are independently selected from hydrogen and optionally substituted alkyl, alkenyl, alkynyl, cycloalkyl, cycloalkenyl, aryl, heterocyclyl, arylalkyl and heterocyclylalkyl, wherein said alkyl may have one or more carbon atoms that are optionally replaced with oxygen atoms.

In still another embodiment, the compound of Formula III is reacted with $HSCH_2C(O)R^3$ to form the compound of Formula IV wherein:
$R^1$ is selected from optionally substituted phenyl, pyridinyl, pyrimidinyl, thienyl or furyl;
$R^2$ is selected from optionally substituted phenyl, pyridinyl, pyrimidinyl, thienyl or furyl;
$R^3$ is selected from —$OR^6$ and —$NR^7R^8$;
$R^4$ and $R^5$ are independently selected from optionally substituted alkyl; and
$R^6$, $R^7$ and $R^8$ are independently selected from hydrogen and optionally substituted lower alkyl, lower alkenyl, 3–6 member ring cycloalkyl, 3–6 member ring cycloalkenyl, phenyl, (phenyl)-lower alkyl and (5- or 6-member heteroaryl)-lower alkyl, wherein said alkyl may have one or more carbon atoms that are optionally replaced with oxygen atoms.

In still another embodiment, the compound of Formula III is reacted with $HSCH_2C(O)R^3$ to form the compound of Formula IV wherein:
one of $R^1$ and $R^2$ is phenyl, pyridinyl, pyrimidinyl, thienyl or furyl optionally substituted with one, two or three radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, alkylsulfonyl, aminosulfonyl, halo, alkoxy and alkylthio;
the other of $R^1$ and $R^2$ is phenyl optionally substituted with one, two or three radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, alkylsulfonyl, aminosulfonyl, halo, alkoxy and alkylthio;
$R^3$ is selected from —$OR^6$ and —$NR^7R^8$;
$R^4$ and $R^5$ are independently selected from optionally substituted alkyl; and
$R^6$, $R^7$ and $R^8$ are independently selected from hydrogen and optionally substituted alkyl, alkenyl, alkynyl, 3–6 member ring cycloalkyl, 3–6 member ring cycloalkenyl, 5- or 6-member ring aryl, 5- or 6-member ring heteroaryl, phenylalkyl and (5- or 6-member heteroaryl)alkyl.

In still another embodiment, the compound of Formula III is reacted with $HSCH_2C(O)R^3$ to form the compound of Formula IV wherein:
one of $R^1$ and $R^2$ is phenyl, pyridinyl, or pyrimidinyl optionally substituted with one, two or three radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, lower alkylsulfonyl, aminosulfonyl, halo, lower alkoxy and lower alkylthio;
the other of $R^1$ and $R^2$ is phenyl optionally substituted with one, two or three radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, lower alkylsulfonyl, aminosulfonyl, halo, lower alkoxy and lower alkylthio;
$R^3$ is selected from —$OR^6$ and —$NR^7R^8$;
$R^4$ and $R^5$ are independently selected from optionally substituted alkyl; and
$R^6$, $R^7$ and $R^8$ are independently selected from hydrogen and optionally substituted lower alkyl, lower alkenyl, 3–6 member ring cycloalkyl, phenyl, 5- or 6-member ring heteroaryl, (phenyl)-lower alkyl, and (5- or 6-member ring heteroaryl)-lower alkyl.

In still another embodiment, the compound of Formula III is reacted with $HSCH_2C(O)R^3$ to form the compound of Formula IV wherein:
- one of $R^1$ and $R^2$ is phenyl, pyridinyl, or pyrimidinyl optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, $C_{1-2}$-alkylsulfonyl, aminosulfonyl, halo, $C_{1-2}$-alkoxy and $C_{1-2}$-alkylthio;
- the other of $R^1$ and $R^2$ is phenyl optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, $C_{1-2}$-alkylsulfonyl, aminosulfonyl, halo, $C_{1-2}$-alkoxy and $C_{1-2}$-alkylthio;
- $R^3$ is selected from $-OR^6$ and $-NR^7R^8$;
- $R^4$ and $R^5$ are independently selected from optionally substituted $C_{1-4}$-alkyl; and
- $R^6$, $R^7$ and $R^8$ are independently selected from hydrogen and optionally substituted $C_{1-3}$-alkyl, $C_{1-3}$-alkenyl, 3–6 member ring cycloalkyl, phenyl, 5- or 6-member ring heteroaryl, (phenyl)$C_{1-3}$-alkyl, (5- or 6-member ring heteroaryl)$C_{1-3}$-alkyl.

In still another embodiment, the compound of Formula III is reacted with $HSCH_2C(O)R^3$ to form the compound of Formula IV wherein:
- one of $R^1$ and $R^2$ is phenyl or pyridinyl optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, methylsulfonyl, aminosulfonyl, fluoro, chloro, bromo, methoxy and methylthio;
- the other of $R^1$ and $R^2$ is phenyl optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, methylsulfonyl, aminosulfonyl, fluoro, chloro, bromo, methoxy and methylthio;
- $R^3$ is selected from $-OR^6$ and $-NR^7R^8$;
- $R^4$ and $R^5$ are independently selected from optionally substituted methyl and ethyl; and
- $R^6$, $R^7$ and $R^8$ are independently selected from hydrogen and optionally substituted methyl, ethyl, propyl, t-butyl, ethenyl, propenyl, propynyl, cyclopropyl, cyclobutyl, cyclopentyl, cyclohexyl, cyclobutenyl, cyclopentenyl, cyclohexenyl, phenyl, pyridinyl, pyrimidinyl, and benzyl.

In still another embodiment, the compound of Formula III is reacted with $HSCH_2C(O)R^3$ to form the compound of Formula IV wherein:
- one of $R^1$ and $R^2$ is phenyl or pyridinyl optionally substituted with one, two or three radicals selected from halo, cyano, $C_{1-2}$-alkyl, $C_{1-2}$-haloalkyl, $C_{1-2}$-alkoxy, $C_{1-2}$-haloalkoxy, $C_{1-2}$-alkylsulfonyl, aminosulfonyl;
- the other of $R^1$ and $R^2$ is phenyl optionally substituted with one, two or three radicals selected from halo, cyano, $C_{1-2}$-alkyl, $C_{1-2}$-haloalkyl, $C_{1-2}$-alkoxy, $C_{1-2}$-haloalkoxy, $C_{1-2}$-alkylsulfonyl, aminosulfonyl;
- $R^3$ is selected from $-OR^6$ and $-NR^7R^8$;
- $R^4$ and $R^5$ are methyl; and
- $R^6$, $R^7$ and $R^8$ are independently selected from hydrogen and optionally substituted $C_{1-3}$-alkyl, $C_{1-3}$-alkenyl, 3–6 member ring cycloalkyl, phenyl, 5- or 6-member ring heteroaryl, (phenyl)$C_{1-3}$-alkyl, and (5- or 6-member ring heteroaryl)$C_{1-3}$-alkyl.

In still another embodiment, the compound of Formula III is reacted with $HSCH_2C(O)R^3$ to form the compound of Formula IV wherein:
- $R^1$ is phenyl or pyridinyl optionally substituted with one, two or three radicals selected from methyl, difluoromethyl, trifluoromethyl, trifluoromethoxy, cyano, methylsulfonyl, aminosulfonyl, fluoro, chloro, bromo, and methoxy;
- $R^2$ is phenyl optionally substituted with one, two or three radicals selected from methyl, difluoromethyl, trifluoromethyl, trifluoromethoxy, cyano, methylsulfonyl, aminosulfonyl, fluoro, chloro, bromo, and methoxy;
- $R^3$ is selected from $-OR^6$ and $-NR^7R^8$;
- $R^4$ and $R^5$ are methyl; and
- $R^6$, $R^7$ and $R^8$ are independently selected from hydrogen and optionally substituted methyl, ethyl, propyl and benzyl.

The reaction of the compound of Formula III with the thioacetic acid, ester of thioacetic acid or amide of thioacetic acid generally is conducted in solution, typically in an organic solvent. The organic solvent may be any suitable solvent such as, for example, a solvent selected from the group consisting of toluene, alcohols and halogenated hydrocarbons. Suitable halogenated hydrocarbons include, but are not limited to, haloalkyls such as 1,2-dichloroethane. The reaction can be carried out over a range of concentrations. In one embodiment, for example, the compound of Formula III is initially present at a concentration of about 1 gram per about 2 to 20 mL of the appropriate solvent. The thioacetic acid, ester of thioacetic acid or amide of thioacetic acid typically is initially present in excess. Preferably, the molar equivalents of thioacetic acid, ester of thioacetic acid or amide of thioacetic acid initially present is at least about 5 to 10 times greater than the molar equivalents of the compound of Formula III initially present. The temperature of the reaction is not critical, but productivity is enhanced by operation at elevated temperature. For example, the reaction advantageously may be carried out by reacting the compound of Formula III with the compound selected from thioacetic acid, esters of thioacetic acid and amides of thioacetic acid in a suitable solvent under reflux conditions. When the reaction is carried out under reflux conditions, it generally is completed within about 4 to 24 hours. The compound of Formula IV is then isolated by removal of solvent and used in the next step of the process. The compounds of Formula IV are novel compounds and have substantial value as intermediates for the preparation of the compounds of Formula V discussed below.

Preparation of the Compound of Formula III

The compound of Formula III can be prepared by any suitable method. In one illustrative process, the compound of Formula III is prepared by reacting an ethanone of Formula I:

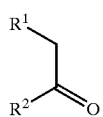

with an acetal of Formula II:

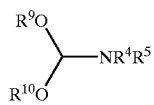

wherein $R^1$, $R^2$, $R^4$ and $R^5$ are as defined for the compound of Formula III, and $R^9$ and $R^{10}$ are optionally substituted alkyl.

The reaction of the ethanone of Formula I with the acetal of Formula II generally is conducted in solution, typically in an organic solvent. The organic solvent may be any suitable solvent, preferably one having a boiling point greater than about 90° C. such as toluene. The reaction can be carried out over a range of concentrations. In one embodiment, for example, the ethanone of Formula I is initially present at a concentration of about 1 gram per about 2 to 20 mL of the appropriate solvent. The acetal of Formula II typically is initially present in excess. Preferably, the molar equivalents of the acetal of Formula II initially present is at least about 1 to 5 times greater than the molar equivalents of the compound of Formula I initially present. The temperature of the reaction is not critical, but productivity is enhanced by operation at elevated temperature. For example, the reaction advantageously may be carried out by reacting the ethanone of Formula I with the acetal of Formula II in a suitable solvent under reflux conditions. When the reaction is carried out under reflux conditions, it generally is completed within about 4 to 24 hours. The compound of Formula II is then isolated by removal of solvent and trituration with hexanes or other appropriate solvents and used in the preparation of the compound of Formula III. The compounds of Formula III are novel compounds and have substantial value as intermediates for the preparation of the compounds of Formula IV.

The ethanones of Formula I can be prepared in accordance with methods disclosed in the technical literature. By way of illustration and not limitation, where the ethanone of Formula I is a deoxybenzoin, such deoxybenzoins can be prepared with specific aromatic ring substitution, for example, through Friedel-Crafts acylation in the manner discussed in C. F. Allen et al., *Org. Synth.* 1943, II, 156; alkylation of cyanohydrins in the manner discussed in Dembech P. et al., *Tetrahedron* 1990, 46, 2999–3006; coupling of organometallic precursors in the manner discussed in S.-H. Kim et al., *Tetrahedron Lett* 1999, 40, 4931–4934; or any other suitable method.

In another embodiment of the invention, (a) an ethanone of Formula I is reacted with an acetal of Formula II to yield a compound of Formula III, and (b) the compound of Formula III is reacted with a compound selected from thioacetic acid, esters of thioacetic acid and amides of thioacetic acid to yield a compound of Formula IV without first isolating the compound of Formula III in purified form. Alternatively, as previously noted, the compound of Formula III can be isolated in substantially purified form before it is reacted with the compound selected from the group consisting thioacetic acid, esters of thioacetic acid and amides of thioacetic acid.

Conversion of Michael Addition Product To Thiophene

The compound of Formula IV:

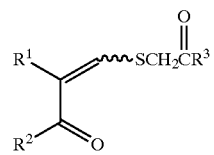

is then reacted with a ring cyclizing reagent to form a compound of Formula V:

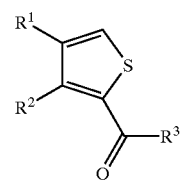

wherein:
$R^1$ is selected from optionally substituted carbocyclyl and heterocyclyl;
$R^2$ is selected from optionally substituted carbocyclyl and heterocyclyl;
$R^3$ is selected from —$OR^6$ and —$NR^7R^8$; and
$R^6$, $R^7$ and $R^8$ are independently selected from hydrogen, hydrocarbyl and heterosubstituted hydrocarbyl.

In another embodiment, the compound of Formula IV is reacted with a ring cyclizing reagent to form a compound of Formula V wherein:
$R^1$ is selected from optionally substituted cycloalkyl, cycloalkenyl, aryl and heteroaryl;
$R^2$ is selected from optionally substituted cycloalkyl, cycloalkenyl, aryl and heteroaryl;
$R^3$ is selected from —$OR^6$ and —$NR^7R^8$; and
$R^6$, $R^7$ and $R^8$ are independently selected from hydrogen and optionally substituted alkyl, alkenyl, alkynyl, cycloalkyl, cycloalkenyl, aryl, heterocyclyl, arylalkyl and heterocyclylalkyl, wherein said alkyl may have one or more carbon atoms that are optionally replaced with oxygen atoms.

In still another embodiment, the compound of Formula IV is reacted with a ring cyclizing reagent to form a compound of Formula V wherein:
$R^1$ is selected from optionally substituted aryl and 5- or 6-membered ring heteroaryl;
$R^2$ is selected from optionally substituted aryl and 5- or 6-membered ring heteroaryl;
$R^3$ is selected from —$OR^6$ and —$NR^7R^8$; and
$R^6$, $R^7$ and $R^8$ are independently selected from hydrogen and optionally substituted alkyl, alkenyl, alkynyl, cycloalkyl, cycloalkenyl, aryl, heterocyclyl, arylalkyl and heterocyclylalkyl, wherein said alkyl may have one or more carbon atoms that are optionally replaced with oxygen atoms.

In still another embodiment, the compound of Formula IV is reacted with a ring cyclizing reagent to form a compound of Formula V wherein:
$R^1$ is selected from optionally substituted phenyl, pyridinyl, pyrimidinyl, thienyl or furyl;

R² is selected from optionally substituted phenyl, pyridinyl, pyrimidinyl, thienyl or furyl;

R³ is selected from —OR⁶ and —NR⁷R⁸; and

R⁶, R⁷ and R⁸ are independently selected from hydrogen and optionally substituted lower alkyl, lower alkenyl, 3–6 member ring cycloalkyl, 3–6 member ring cycloalkenyl, phenyl, (phenyl)-lower alkyl and (5- or 6-member heteroaryl)-lower alkyl, wherein said alkyl may have one or more carbon atoms that are optionally replaced with oxygen atoms.

In still another embodiment, the compound of Formula IV is reacted with a ring cyclizing reagent to form a compound of Formula V wherein:

one of R¹ and R² is phenyl, pyridinyl, pyrimidinyl, thienyl or furyl optionally substituted with one, two or three radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, alkylsulfonyl, aminosulfonyl, halo, alkoxy and alkylthio;

the other of R¹ and R² is phenyl optionally substituted with one, two or three radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, alkylsulfonyl, aminosulfonyl, halo, alkoxy and alkylthio;

R³ is selected from —OR⁶ and —NR⁷R⁸; and

R⁶, R⁷ and R⁸ are independently selected from hydrogen and optionally substituted alkyl, alkenyl, alkynyl, 3–6 member ring cycloalkyl, 3–6 member ring cycloalkenyl, 5- or 6-member ring aryl, 5- or 6-member ring heteroaryl, phenylalkyl and (5- or 6-member heteroaryl)alkyl.

In still another embodiment, the compound of Formula IV is reacted with a ring cyclizing reagent to form a compound of Formula V wherein:

one of R¹ and R² is phenyl, pyridinyl, or pyrimidinyl optionally substituted with one, two or three radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, lower alkylsulfonyl, aminosulfonyl, halo, lower alkoxy and lower alkylthio;

the other of R¹ and R² is phenyl optionally substituted with one, two or three radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, lower alkylsulfonyl, aminosulfonyl, halo, lower alkoxy and lower alkylthio;

R³ is selected from —OR⁶ and —NR⁷R⁸; and

R⁶, R⁷ and R⁸ are independently selected from hydrogen and optionally substituted lower alkyl, lower alkenyl, 3–6 member ring cycloalkyl, phenyl, 5- or 6-member ring heteroaryl, (phenyl)-lower alkyl, and (5- or 6-member heteroaryl)-lower alkyl.

In still another embodiment, the compound of Formula IV is reacted with a ring cyclizing reagent to form a compound of Formula V wherein:

one of R¹ and R² is phenyl, pyridinyl, or pyrimidinyl optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, $C_{1-2}$-alkylsulfonyl, aminosulfonyl, halo, $C_{1-2}$-alkoxy and $C_{1-2}$-alkylthio;

the other of R¹ and R² is phenyl optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, $C_{1-2}$-alkylsulfonyl, aminosulfonyl, halo, $C_{1-2}$-alkoxy and $C_{1-2}$-alkylthio;

R³ is selected from —OR⁶ and —NR⁷R⁸;

R⁴ and R⁵ are independently selected from optionally substituted $C_{1-4}$-alkyl; and R⁶, R⁷ and R⁸ are independently selected from hydrogen and optionally substituted $C_{1-3}$-alkyl, $C_{1-3}$-alkenyl, 3–6 member ring cycloalkyl, phenyl, 5- or 6-member ring heteroaryl, (phenyl)$C_{1-3}$-alkyl, (5- or 6-member ring heteroaryl)$C_{1-3}$-alkyl.

In still another embodiment, the compound of Formula IV is reacted with a ring cyclizing reagent to form a compound of Formula V wherein:

one of R¹ and R² is phenyl or pyridinyl optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, methylsulfonyl, aminosulfonyl, fluoro, chloro, bromo, methoxy and methylthio;

the other of R¹ and R² is phenyl optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, methylsulfonyl, aminosulfonyl, fluoro, chloro, bromo, methoxy and methylthio;

R³ is selected from —OR⁶ and —NR⁷R⁸; and

R⁶, R⁷ and R⁸ are independently selected from hydrogen and optionally substituted methyl, ethyl, propyl, t-butyl, ethenyl, propenyl, propynyl, cyclopropyl, cyclobutyl, cyclopentyl, cyclohexyl, cyclobutenyl, cyclopentenyl, cyclohexenyl, phenyl, pyridinyl, pyrimidinyl, and benzyl.

In still another embodiment, the compound of Formula IV is reacted with a ring cyclizing reagent to form a compound of Formula V wherein:

one of R¹ and R² is phenyl or pyridinyl optionally substituted with one, two or three radicals selected from halo, cyano, $C_{1-2}$-alkyl, $C_{1-2}$-haloalkyl, $C_{1-2}$-alkoxy, $C_{1-2}$-haloalkoxy, $C_{1-2}$-alkylsulfonyl, aminosulfonyl;

the other of R¹ and R² is phenyl optionally substituted with one, two or three radicals selected from halo, cyano, $C_{1-2}$-alkyl, $C_{1-2}$-haloalkyl, $C_{1-2}$-alkoxy, $C_{1-2}$-haloalkoxy, $C_{1-2}$-alkylsulfonyl, aminosulfonyl;

R³ is selected from —OR⁶ and —NR⁷R⁸; and

R⁶, R⁷ and R⁸ are independently selected from hydrogen and optionally substituted $C_{1-3}$-alkyl, $C_{1-3}$-alkenyl, 3–6 member ring cycloalkyl, phenyl, 5- or 6-member ring heteroaryl, (phenyl)$C_{1-3}$-alkyl, and (5- or 6-member ring heteroaryl)$C_{1-3}$-alkyl.

In still another embodiment, the compound of Formula IV is reacted with a ring cyclizing reagent to form a compound of Formula V wherein:

R¹ is phenyl or pyridinyl optionally substituted with one, two or three radicals selected from methyl, difluoromethyl, trifluoromethyl, trifluoromethoxy, cyano, methylsulfonyl, aminosulfonyl, fluoro, chloro, bromo, and methoxy;

R² is phenyl optionally substituted with one, two or three radicals selected from methyl, difluoromethyl, trifluoromethyl, trifluoromethoxy, cyano, methylsulfonyl, aminosulfonyl, fluoro, chloro, bromo, and methoxy;

R³ is selected from —OR⁶ and —NR⁷R⁸; and

R⁶, R⁷ and R⁸ are independently selected from hydrogen and optionally substituted methyl, ethyl, propyl and benzyl.

The reaction of the compound of Formula IV with the cyclizing reagent generally is conducted in solution, typically in an organic solvent. The organic solvent may be any suitable solvent such as a solvent selected from the group consisting of alcohols, such as methanol, and ethereal solvents. Suitable ring cyclizing reagents include, but are not limited to, alkoxides, particularly alkoxide bases. Typical alkoxide bases useful as ring cyclizing reagents include alkali metal alkoxides such as sodium methoxide and potassium tert-butoxide. The reaction advantageously may be carried out by reacting the compound of Formula IV with an alkoxide base, preferably an alkali metal alkoxide such as sodium methoxide, in an alcohol solvent, preferably methanol. The reaction can be carried out over a range of concentrations. In one embodiment, for example, the compound of Formula IV is initially present at a concentration of about 1 to 10 g per mL solvent. The cyclizing reagent typically is initially present in excess. Preferably, the molar equivalents of the cyclizing reagent initially present is at least about 3 to 5 times greater than the molar equivalents of the compound of Formula IV initially present. The temperature of the reaction is not critical, but productivity is enhanced by operation at elevated temperature up to the reflux temperature of the reaction solvent. When the reaction is carried out in methanol with sodium methoxide as the cyclizing agent, it generally is completed within about two hours. Michael addition of the methylthioglycolate in refluxing 1,2-dichloroethane, for example, affords a mixture of E and Z vinylogous thioesters as well as some of the desired thiophenes. Removal of the solvent and replacement with, for example, methanol, followed by the addition of, for example, sodium methoxide affords the 3,4-diarylthiophenes after about 1 to 16 hours of mixing.

The compound of Formula V is then isolated by crystallization, distillation, chromatography, or other suitable method and functionalized as desired. The compounds of Formula V are novel compounds and have substantial value as final products or as intermediates for the preparation of thiophene derivatives and analogs of compounds of Formula V. The regioselective placement of the single ester or amido functionality relative to the 3,4-di(carbocyclyl or heterocyclyl)moieties of the thiophene permits the direct use of the thiophene in subsequent ring modification reactions without the need for separation of isomeric mixtures as typically required in conventional processes.

In one embodiment, (a) the compound of Formula V is prepared by reacting a compound of Formula IV with a ring cyclizing reagent; and (b) the compound of Formula IV is prepared by reacting a compound of Formula III with a compound selected from the group consisting of thioacetic acid, esters of thioacetic acid and amides of thioacetic acid, as previously discussed.

In another embodiment (a) the compound of Formula V is prepared by reacting a compound of Formula IV with a ring cyclizing reagent; (b) the compound of Formula IV is prepared by reacting a compound of Formula III with a compound selected from the group consisting of thioacetic acid, esters of thioacetic acid and amides of thioacetic acid, as previously discussed; and (c) the compound of Formula III is prepared by reacting an ethanone of Formula I with an acetal of Formula II, as previously discussed.

In still another embodiment, (a) an ethanone of Formula I is reacted with an acetal of Formula II to prepare a compound of Formula III, (b) the compound of formula III is reacted with a compound selected from thioacetic acid, esters of thioacetic acid and amides of thioacetic acid to prepare a compound of formula IV, as previously discussed, and (c) the compound of Formula V is prepared by reacting a compound of Formula IV with a ring cyclizing reagent, without first isolating one or both of the compounds of Formulae III and IV in purified form for use in the next step of the process. Alternatively, the compounds of Formulae III and IV each can be isolated in substantially purified form before they are used in the next step of the reaction.

Preparation of 3,4-Diphenylthiophenes from Deoxybenzoins

In one embodiment of specific interest, the present invention comprises a process for the regioselective preparation of 3,4-diphenylthiophenes. In general, a deoxybenzoin comprising two differently substituted phenyl moieties is prepared. For example, one phenyl moiety is substituted with one or more functional groups and the other phenyl moiety is unsubstituted. Alternatively, each phenyl moiety is substituted with one or more functional groups, but has a different substitution pattern than the other phenyl moiety. A Michael acceptor is introduced into the primary carbon chain of the deoxybenzoin to yield a deoxybenzoin comprising at least two double bonds conjugated with the same or different electron withdrawing groups. This deoxybenzoin is reacted with thioacetic acid or an ester or amide of thioacetic acid to yield a Michael addition product in a nucleophilic addition reaction. Finally, the Michael addition product is cyclized to yield a 3,4-diphenylthiophene that can be further functionalized if desired.

Scheme I-A illustrates a preferred embodiment of the overall process described above:

Scheme I-A

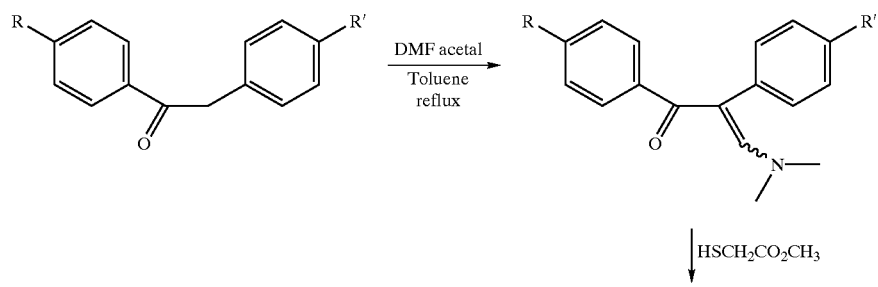

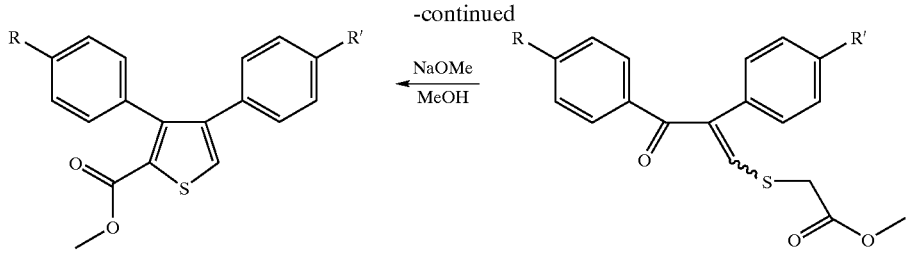

Preparation of [(Methylsulfonyl or Aminosulfonyl)phenyl]-Thiophenes

In one embodiment of particular interest, the present invention comprises a process for the regioselective preparation of 3,4-di(carbocyclyl or heterocyclyl)thiophenes wherein the thiophene is substituted at the 3- or 4-position with a phenyl group comprising a methylsulfonyl or aminosulfonyl group. Preferably, the thiophene is substituted at the 3- or 4-position with a 4-methylsulfonylphenyl, 4-aminosulfonylphenyl, (3-fluoro-4-methylsulfonyl)phenyl, or (3-fluoro-4-aminosulfonyl)phenyl group.

The present process can be used to prepare compounds of Formula V that are encompassed within, or that can be used as intermediates in the preparation of, a group of compounds of particular interest having Formula VI:

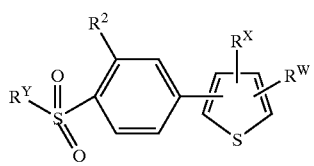

VI wherein:
- $R^W$ is cyclohexyl, pyridinyl, or phenyl, wherein said cyclohexyl, pyridinyl, and phenyl may be optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, halo, $C_{1-2}$-alkoxy and $C_{1-3}$-alkylthio;
- $R^X$ is a radical selected from hydrido, halo, $C_{1-2}$-alkyl, $C_{2-3}$-alkenyl, $C_{2-3}$-alkynyl, oxo, cyano, carboxyl, cyano-$C_{1-3}$-alkyl, heterocyclyloxy, $C_{1-3}$-alkoxy, $C_{1-3}$-alkylthio, alkylcarbonyl, cycloalkyl, phenyl, $C_{1-3}$-haloalkyl, heterocyclyl, cycloalkenyl, phenyl-$C_{1-3}$-alkyl, heterocyclyl-$C_{1-3}$-alkyl, $C_{1-3}$-alkylthio-$C_{1-3}$-alkyl, $C_{1-3}$-hydroxyalkyl, $C_{1-3}$-alkoxycarbonyl, phenylcarbonyl, phenyl-$C_{1-3}$-alkylcarbonyl, phenyl-$C_{2-3}$-alkenyl, $C_{1-3}$-alkoxy-$C_{1-3}$-alkyl, phenylthio-$C_{1-3}$-alkyl, phenyloxyalkyl, alkoxyphenylalkoxyalkyl, alkoxycarbonylalkyl, aminocarbonyl, aminocarbonyl-$C_{1-3}$-alkyl, $C_{1-3}$-alkylaminocarbonyl, N-phenylaminocarbonyl, N-($C_{1-3}$-alkyl)-N-phenylaminocarbonyl, $C_{1-3}$-alkylaminocarbonyl-$C_{1-3}$-alkyl, carboxy-$C_{1-3}$-alkyl, $C_{1-3}$-alkylamino, N-arylamino, N-aralkylamino, N-($C_{1-3}$-alkyl)-N-aralkylamino, N-($C_{1-3}$-alkyl)-N-arylamino, amino-$C_{1-3}$-alkyl, $C_{1-3}$-alkylaminoalkyl, N-phenylamino-$C_{1-3}$-alkyl, N-phenyl-$C_{1-3}$-alkylaminoalkyl, N-($C_{1-3}$-alkyl)-N-(phenyl-$C_{1-3}$-alkyl)amino-$C_{1-3}$-alkyl, N-($C_{1-3}$-alkyl)-N-phenylamino-$C_{1-3}$-alkyl, phenyloxy, phenylalkoxy, phenylthio, phenyl-$C_{1-3}$-alkylthio, $C_{1-3}$-alkylsulfinyl, $C_{1-3}$-alkylsulfonyl, aminosulfonyl, $C_{1-3}$-alkylaminosulfonyl, N-phenylaminosulfonyl, phenylsulfonyl, and N-($C_{1-3}$-alkyl)-N-phenylaminosulfonyl; and
- $R^Y$ is methyl or amino; and
- $R^Z$ is hydrogen or fluoro; or a pharmaceutically-acceptable salt, tautomer or prodrug thereof.

In another embodiment, the compounds of Formula V prepared in accordance with the present process are encompassed within, or can be used as intermediates in the preparation of, compounds of Formula VI wherein:
- $R^W$ is cyclohexyl, pyridinyl, or phenyl, wherein said cyclohexyl, pyridinyl, and phenyl may be optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, halo, $C_{1-2}$-alkoxy and $C_{1-3}$-alkylthio;
- $R^X$ is a radical selected from hydrido, halo, $C_{1-2}$-alkyl, $C_{2-3}$-alkenyl, $C_{2-3}$-alkynyl, oxo, cyano, carboxyl, cyano-$C_{1-3}$-alkyl, (5- or 6-member ring heterocyclyl)oxy, $C_{1-3}$-alkoxy, $C_{1-3}$-alkylthio, $C_{1-3}$-alkylcarbonyl, $C_{3-6}$-cycloalkyl, phenyl, $C_{1-3}$-haloalkyl, 5- or 6-member ring heterocyclyl, $C_{3-6}$-cycloalkenyl, phenyl-$C_{1-3}$-alkyl, (5- or 6-member ring heterocyclyl)-$C_{1-3}$-alkyl, $C_{1-3}$-alkylthio-$C_{1-3}$-alkyl, $C_{1-3}$-hydroxyalkyl, $C_{1-3}$-alkoxycarbonyl, phenylcarbonyl, phenyl-$C_{1-3}$-alkylcarbonyl, phenyl-$C_{2-3}$-alkenyl, $C_{1-3}$-alkoxy-$C_{1-3}$-alkyl, phenylthio-$C_{1-3}$-alkyl, phenyloxy-$C_{1-3}$-alkyl, $C_{1-3}$-alkoxyphenyl-$C_{1-3}$-alkoxy-$C_{1-3}$-alkyl, $C_{1-3}$-alkoxycarbonyl-$C_{1-3}$-alkyl, aminocarbonyl, aminocarbonyl-$C_{1-3}$-alkyl, $C_{1-3}$-alkylaminocarbonyl, N-phenylaminocarbonyl, N-($C_{1-3}$-alkyl)-N-phenylaminocarbonyl, $C_{1-3}$-alkylaminocarbonyl-$C_{1-3}$-alkyl, carboxy-$C_{1-3}$-alkyl, $C_{1-3}$-alkylamino, N-phenylamino, N-(phenyl-$C_{1-3}$-alkyl)amino, N-($C_{1-3}$-alkyl)-N-(phenyl-$C_{1-3}$-alkyl)amino, N-($C_{1-3}$-alkyl)-N-phenylamino, amino-$C_{1-3}$-alkyl, $C_{1-3}$-alkylamino-$C_{1-3}$-alkyl, N-phenylamino-$C_{1-3}$-alkyl, N-phenyl-$C_{1-3}$-alkylamino-$C_{1-3}$-alkyl, N-($C_{1-3}$-alkyl)-N-phenyl-$C_{1-3}$-alkylamino-$C_{1-3}$-alkyl, N-($C_{1-3}$-alkyl)-N-phenylamino-$C_{1-3}$-alkyl, phenyloxy, phenyl-$C_{1-3}$-alkoxy, phenylthio, phenyl-$C_{1-3}$-alkylthio, $C_{1-3}$-alkylsulfinyl, $C_{1-3}$-alkylsulfonyl, aminosulfonyl, $C_{1-3}$-alkylaminosulfonyl, N-phenylaminosulfonyl, phenylsulfonyl, and N-($C_{1-3}$-alkyl)-N-phenylaminosulfonyl; and
- $R^Y$ is methyl or amino; and
- $R^Z$ is hydrogen or fluoro; or a pharmaceutically-acceptable salt, tautomer or prodrug thereof.

In still another embodiment, the compounds of Formula V prepared in accordance with the present process are encompassed within, or can be used as intermediates in the preparation of, compounds of Formula VI wherein $R^W$ is cyclohexyl, pyridinyl, or phenyl, wherein said cyclohexyl, pyridinyl, and phenyl may be optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, fluoro, chloro, bromo, methoxy and methylthio.

In still another embodiment, the compounds of Formula V prepared in accordance with the present process are encompassed within, or can be used as intermediates in the preparation of, compounds of Formula VI wherein $R^X$ is a radical selected from hydrido, fluoro, chloro, bromo, methyl, oxo, cyano, carboxyl, cyanomethyl, methoxy, methylthio, methylcarbonyl, phenyl, trifluoromethyl, difluoromethyl, phenylmethyl, methylthiomethyl, hydroxymethyl, methoxycarbonyl, ethoxycarbonyl, phenylcarbonyl, phenylmethylcarbonyl, methoxymethyl, phenylthiomethyl, phenyloxymethyl, methoxyphenylmethoxymethyl, methoxycarbonylmethyl, aminocarbonyl, aminocarbonylmethyl, methylaminocarbonyl, N-phenylaminocarbonyl, N-methyl-N-phenylaminocarbonyl, methylaminocarbonylmethyl, carboxymethyl, methylamino, N-phenylamino, N-(phenylmethyl)amino, N-methyl-N-(phenylmethyl)amino, N-methyl-N-phenylamino, aminomethyl, methylaminomethyl, N-phenylaminomethyl, N-phenylmethylaminomethyl, N-methyl-N-phenylmethylaminomethyl, N-methyl-N-phenylaminomethyl, phenyloxy, phenylmethoxy, phenylthio, phenylmethylthio, methylsulfinyl, methylsulfonyl, aminosulfonyl, methylaminosulfonyl, N-phenylaminosulfonyl, phenylsulfonyl, and N-methyl-N-phenylaminosulfonyl.

In still another embodiment, the compounds of Formula V prepared in accordance with the present process are encompassed within, or can be used as intermediates in the preparation of, compounds of Formula VI wherein:
$R^W$ is cyclohexyl or phenyl, wherein said cyclohexyl and phenyl may be optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, fluoro, chloro, bromo, methoxy and methylthio; and
$R^X$ is a radical selected from hydrido, fluoro, chloro, bromo, methyl, oxo, cyano, carboxyl, cyanomethyl, methoxy, methylthio, methylcarbonyl, phenyl, trifluoromethyl, difluoromethyl, phenylmethyl, methylthiomethyl, hydroxymethyl, methoxycarbonyl, ethoxycarbonyl, phenylcarbonyl, phenylmethylcarbonyl, methoxymethyl, phenylthiomethyl, phenyloxymethyl, methoxyphenylmethoxymethyl, methoxycarbonylmethyl, aminocarbonyl, aminocarbonylmethyl, methylaminocarbonyl, N-phenylaminocarbonyl, N-methyl-N-phenylaminocarbonyl, methylaminocarbonylmethyl, carboxymethyl, methylamino, N-phenylamino, N-(phenylmethyl)amino, N-methyl-N-(phenylmethyl)amino, N-methyl-N-phenylamino, aminomethyl, methylaminomethyl, N-phenylaminomethyl, N-phenylmethylaminomethyl, N-methyl-N-phenylmethylaminomethyl, N-methyl-N-phenylaminomethyl, phenyloxy, phenylmethoxy, phenylthio, phenylmethylthio, methylsulfinyl, methylsulfonyl, aminosulfonyl, methylaminosulfonyl, N-phenylaminosulfonyl, phenylsulfonyl, and N-methyl-N-phenylaminosulfonyl.

In still another embodiment, the compounds of Formula V prepared in accordance with the present process are encompassed within, or can be used as intermediates in the preparation of, compounds of Formula VIA:

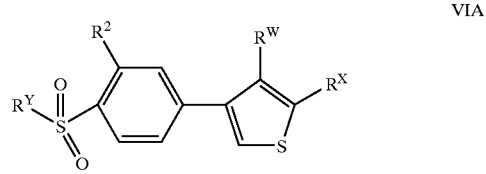

wherein $R^W$, $R^X$, $R^Y$ and $R^Y$ are as defined above.

In still another embodiment, the compounds of Formula V prepared in accordance with the present process are encompassed within, or can be used as intermediates in the preparation of, compounds of Formula VIA wherein:
$R^W$ is cyclohexyl or phenyl, wherein said cyclohexyl and phenyl may be optionally substituted with one, two or three radicals selected from halo, cyano, $C_{1-2}$-alkyl, $C_{1-2}$-haloalkyl, $C_{1-2}$-alkoxy, and $C_{1-2}$-haloalkoxy; and
$R^X$ is a radical selected from hydrido, halogen, $C_{1-2}$-alkyl, $C_{1-3}$-alkoxy, $C_{1-3}$-alkylcarbonyl, $C_{1-3}$-haloalkyl, $C_{1-3}$-hydroxyalkyl, and $C_{1-3}$-alkoxycarbonyl.

In still another embodiment, the compounds of Formula V prepared in accordance with the present process are encompassed within, or can be used as intermediates in the preparation of, compounds of Formula VIA wherein:
$R^W$ is cyclohexyl or phenyl, wherein said cyclohexyl and phenyl may be optionally substituted with one, two or three radicals selected from methyl, difluoromethyl, trifluoromethyl, trifluoromethoxy, cyano, fluoro, chloro, bromo, iodo and methoxy; and
$R^X$ is a radical selected from hydrido, chloro, fluoro, bromo, cyano, methyl, methoxy, methylcarbonyl, trifluoromethyl, difluoromethyl, hydroxymethyl, and methoxycarbonyl.

In still another embodiment, the compounds of Formula V prepared in accordance with the present process are used as intermediates in the preparation of a compound selected from the group consisting of the following compounds:
3-phenyl-4-[3-fluoro-4-(methylsulfonyl)phenyl]thiophene;
3-(3-chlorophenyl)-4-[3-fluoro-4-(methylsulfonyl) phenyl]thiophene;
3-(4-chlorophenyl)-4-[3-fluoro-4-(methylsulfonyl)phenyl]thiophene;
3-(3-bromophenyl)-4-[3-fluoro-4-(methylsulfonyl)phenyl]thiophene;
3-(4-bromophenyl)-4-[3-fluoro-4-(methylsulfonyl)phenyl]thiophene;
3-(3-fluorophenyl)-4-[3-fluoro-4-(methylsulfonyl)phenyl]thiophene;
3-(4-fluorophenyl)-4-[3-fluoro-4-(methylsulfonyl)phenyl]thiophene;
3-(3-methylphenyl)-4-[3-fluoro-4-(methylsulfonyl)phenyl]thiophene;
3-(4-methylphenyl)-4-[3-fluoro-4-(methylsulfonyl)phenyl]thiophene;
3-(3-cyanophenyl)-4-[3-fluoro-4-(methylsulfonyl)phenyl]thiophene;
3-(4-cyanophenyl)-4-[3-fluoro-4-(methylsulfonyl)phenyl]thiophene;

3-(3-trifluoromethylphenyl)-4-[3-fluoro-4-(methylsulfonyl)phenyl]thiophene;
3-(4-trifluoromethylphenyl)-4-[3-fluoro-4 (methylsulfonyl)phenyl]thiophene;
3-(3-trifluoromethoxyphenyl)-4-[3-fluoro-4-(methylsulfonyl)phenyl]thiophene;
3-(4-trifluoromethoxyphenyl)-4-[3-fluoro-4-(methylsulfonyl)phenyl]thiophene;
3-(3,4-dichlorophenyl)-4-[3-fluoro-4-(methylsulfonyl)phenyl]thiophene;
3-(3,4-dibromophenyl)-4-[3-fluoro-4-(methylsulfonyl)phenyl]thiophene;
3-(3,4-difluorophenyl)-4-[3-fluoro-4-(methylsulfonyl)phenyl]thiophene;
3-(3,5-dichlorophenyl)-4-[3-fluoro-4-(methylsulfonyl)phenyl]thiophene;
3-(3,5-dibromophenyl)-4-[3-fluoro-4-(methylsulfonyl)phenyl]thiophene;
3-(3,5-difluorophenyl)-4-[3-fluoro-4-(methylsulfonyl)phenyl]thiophene;
3-(3,4-dimethylphenyl)-4-[3-fluoro-4-(methylsulfonyl)phenyl]thiophene;
3-(3,5-dimethylphenyl)-4-[3-fluoro-4-(methylsulfonyl)phenyl]thiophene;
3-(3-methyl-4-chlorophenyl)-4-[3-fluoro-4-(methylsulfonyl)phenyl]thiophene;
3-(4-methyl-3-chlorophenyl)-4-[3-fluoro-4-(methylsulfonyl)phenyl]thiophene;
3-(3-methyl-4-fluorophenyl)-4-[3-fluoro-4-(methylsulfonyl)phenyl]thiophene;
3-(4-methyl-3-fluorophenyl)-4-[3-fluoro-4-(methylsulfonyl)phenyl]thiophene;
3-(3-methyl-4-bromophenyl)-4-[3-fluoro-4-(methylsulfonyl)phenyl]thiophene;
3-(4-methyl-3-bromophenyl)-4-[3-fluoro-4-(methylsulfonyl)phenyl]thiophene;
3-(3-methyl-4-trifluoromethylphenyl)-4-[3-fluoro-4-(methylsulfonyl)phenyl]thiophene;
3-(4-methyl-3-trifluoromethylphenyl)-4-[3-fluoro-4-(methylsulfonyl)phenyl]thiophene;
3-(3-methyl-4-trifluoromethoxyphenyl)-4-[3-fluoro-4-(methylsulfonyl)phenyl]thiophene;
3-(4-methyl-3-trifluoromethoxyphenyl)-4-[3-fluoro-4-(methylsulfonyl)phenyl]thiophene;
3-(3-cyano-4-methylphenyl)-4-[3-fluoro-4-(methylsulfonyl)phenyl]thiophene;
3-(4-cyano-3-methylphenyl)-4-[3-fluoro-4-(methylsulfonyl)phenyl]thiophene;
3-(3-chloro-4-methoxyphenyl)-4-[3-fluoro-4-(methylsulfonyl)phenyl]thiophene;
3-(4-chloro-3-methoxyphenyl)-4-[3-fluoro-4-(methylsulfonyl)phenyl]thiophene;
3-(2-methylpyridin-6-yl)-4-[3-fluoro-4-(methylsulfonyl)phenyl]thiophene;
3-(2-methylthiazol-4-yl)-4-[3-fluoro-4-(methylsulfonyl)phenyl]thiophene;
3-(4-methylthiazol-2-yl)-4-[3-fluoro-4-(methylsulfonyl)phenyl]thiophene;
3-(2-methylpyridin-3-yl)-4-[3-fluoro-4-(methylsulfonyl)phenyl]thiophene;
3-(2-methylpyridin-3-yl)-4-[3-fluoro-4-(methylsulfonyl)phenyl]thiophene;
3-(3-pyridinyl)-4-[3-fluoro-4-(methylsulfonyl)phenyl]thiophene;
3-(5-methylpyridin-3-yl)-4-[3-fluoro-4-(methylsulfonyl)phenyl]thiophene;
3-(2-methylpyridin-3-yl)-4-[3-fluoro-4-(methylsulfonyl)phenyl]thiophene;
3-cyclohexyl-4-[3-fluoro-4-(methylsulfonyl)phenyl]thiophene;
3-cyclopentyl-4-[3-fluoro-4-(methylsulfonyl)phenyl]thiophene;
2-fluoro-4-[4-phenyl-3-thiophenyl]benzenesulfonamide;
2-fluoro-4-[4-(3-chlorophenyl)-3-thiophenyl]benzenesulfonamide;
2-fluoro-4-[4-(4-chlorophenyl)-3-thiophenyl]benzenesulfonamide;
2-fluoro-4-[4-(3-bromophenyl)-3-thiophenyl]benzenesulfonamide;
2-fluoro-4-[4-(4-bromophenyl)-3-thiophenyl]benzenesulfonamide;
2-fluoro-4-[4-(3-fluorophenyl)-3-thiophenyl]benzenesulfonamide;
2-fluoro-4-[4-(4-fluorophenyl)-3-thiophenyl]benzenesulfonamide;
2-fluoro-4-[4-(3-methylphenyl)-3-thiophenyl]benzenesulfonamide;
2-fluoro-4-[4-(4-methylphenyl)-3-thiophenyl]benzenesulfonamide;
2-fluoro-4-[4-(3-cyanophenyl)-3-thiophenyl]benzenesulfonamide;
2-fluoro-4-[4-(4-cyanophenyl)-3-thiophenyl]benzenesulfonamide;
2-fluoro-4-[4-(3-trifluoromethylphenyl)-3-thiophenyl]benzenesulfonamide;
2-fluoro-4-[4-(4-trifluoromethylphenyl)-3-thiophenyl]benzenesulfonamide;
2-fluoro-4-[4-(3-trifluoromethoxyphenyl)-3-thiophenyl]benzenesulfonamide;
2-fluoro-4-[4-(4-trifluoromethoxyphenyl)-3-thiophenyl]benzenesulfonamide;
2-fluoro-4-[4-(3,4-dichlorophenyl)-3-thiophenyl]benzenesulfonamide;
2-fluoro-4-[4-(3,4-dibromophenyl)-3-thiophenyl]benzenesulfonamide
2-fluoro-4-[4-(3,4-difluorophenyl)-3-thiophenyl]benzenesulfonamide;
2-fluoro-4-[4-(3,5-dichlorophenyl)-3-thiophenyl]benzenesulfonamide;
2-fluoro-4-[4-(3,5-dibromophenyl)-3-thiophenyl]benzenesulfonamide;
2-fluoro-4-[4-(3,5-difluorophenyl)-3-thiophenyl]benzenesulfonamide;
2-fluoro-4-[4-(3,4-dimethylphenyl)-3-thiophenyl]benzenesulfonamide;
2-fluoro-4-[4-(3,5-dimethylphenyl)-3-thiophenyl]benzenesulfonamide;
2-fluoro-4-[4-(3-methyl-4-chlorophenyl)-3-thiophenyl]benzenesulfonamide;
2-fluoro-4-[4-(4-methyl-3-chlorophenyl)-3-thiophenyl]benzenesulfonamide;
2-fluoro-4-[4-(3-methyl-4-fluorophenyl)-3-thiophenyl]benzenesulfonamide;
2-fluoro-4-[4-(4-methyl-3-fluorophenyl)-3-thiophenyl]benzenesulfonamide;
2-fluoro-4-[4-(3-methyl-4-bromophenyl)-3-thiophenyl]benzenesulfonamide;
2-fluoro-4-[4-(4-methyl-3-bromophenyl)-3-thiophenyl]benzenesulfonamide;
2-fluoro-4-[4-(3-methyl-4-trifluoromethylphenyl)-3-thiophenyl]benzene-sulfonamide;
2-fluoro-4-[4-(4-methyl-3-trifluoromethylphenyl)-3-thiophenyl]benzene-sulfonamide;
2-fluoro-4-[4-(3-methyl-4-trifluoromethoxyphenyl)-3-thiophenyl]benzenesulfonamide;

2-fluoro-4-[4-(4-methyl-3-trifluoromethoxyphenyl)-3-thiophenyl]benezenesulfonamide;
2-fluoro-4-[4-(3-cyano-4-methylphenyl)-3-thiophenyl]benezenesulfonamide;
2-fluoro-4-[4-(4-cyano-3-methylphenyl)-3-thiophenyl]benezenesulfonamide;
2-fluoro-4-[4-(3-chloro-4-methoxyphenyl)-3-thiophenyl]benezenesulfonamide;
2-fluoro-4-[4-(4-chloro-3-methoxyphenyl)-3-thiophenyl]benezenesulfonamide;
2-fluoro-4-[4-(2-methylpyridin-6-yl)-3-thiophenyl]benezenesulfonamide;
2-fluoro-4-[4-(2-methylthiazol-4-yl)-3-thiophenyl]benezenesulfonamide;
2-fluoro-4-[4-(4-methylthiazol-2-yl)-3-thiophenyl]benezenesulfonamide;
2-fluoro-4-[4-(2-methylpyridin-3-yl)-3-thiophenyl]benezenesulfonamide;
2-fluoro-4-[4-(2-methylpyridin-3-yl)-3-thiophenyl]benezenesulfonamide;
2-fluoro-4-[4-(3-pyridinyl)-3-thiophenyl]benezenesulfonamide;
2-fluoro-4-[4-(5-methylpyridin-3-yl)-3-thiophenyl]benezenesulfonamide;
2-fluoro-4-[4-(2-methylpyridin-3-yl)-3-thiophenyl]benezenesulfonamide;
2-fluoro-4-[4-cyclohexyl-3-thiophenyl]benezenesulfonamide;
2-fluoro-4-[4-cyclopentyl-3-thiophenyl]benezenesulfonamide;
and the pharmaceutically-acceptable salts, tautomers and prodrugs thereof.

Definitions

The term "hydrido" denotes a single hydrogen atom (H). This hydrido radical may be attached, for example, to an oxygen atom to form a hydroxyl radical or two hydrido radicals may be attached to a carbon atom to form a methylene ($—CH_2—$) radical.

Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to three carbon atoms.

The term "alkenyl" embraces linear or branched radicals having at least one carbon—carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl.

The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like.

The terms "alkenyl" and "lower alkenyl", embrace radicals having "cis" and "trans" orientations, or alternatively, "E" and "Z" orientations.

The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "cyanoalkyl" embraces linear or branched alkyl radicals having one to about ten carbon atoms any one of which may be substituted with one cyano radicals. More preferred cyanoalkyl radicals are "lower cyanoalkyl" radicals having one to six carbon atoms and one cyano radical. Even more preferred are lower cyanoalkyl radicals having one to three carbon atoms. Examples of such radicals include cyanomethyl.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have one to three substituents such as lower alkyl, hydroxy, halo, haloalkyl, nitro, cyano, alkoxy and lower alkylamino.

The term "heterocyclyl" or "heterocyclo" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic groups containing 1 to 4 nitrogen atoms [e.g. pyrrolidinyl, imidazolidinyl, piperidino, piperazinyl]; saturated 3 to 6-membered heteromonocyclic groups containing 1 to 2 oxygen atoms and 1 to 3 nitrogen atoms [e.g. morpholinyl]; saturated 3 to 6-membered heteromonocyclic groups containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl]; unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated condensed heterocyclic groups containing 1 to 2 oxygen atoms and 1 to 3 nitrogen atoms [e.g. benzoxazolyl, benzoxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]; unsaturated condensed heterocyclic groups containing 1 to 2 sulfur atoms and 1 to 3 nitrogen atoms [e.g., benzothiazolyl, benzothiadiazolyl] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents such as lower alkyl, hydroxy, oxo, amino and lower alkylamino.

Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. Even more preferred heteroaryl radicals are 5- or 6-membered heteroaryl, containing one or two heteroatoms selected from sulfur nitrogen and oxygen, selected from thienyl, furanyl, pyrrolyl, thiazolyl, oxazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, ethylsulfonyl and propylsulfonyl. "Haloalkylsulfonyl" embraces haloalkyl radicals attached to a sulfonyl radical, where haloalkyl is defined as above. More preferred haloalkylsulfonyl radicals are "lower haloalkylsulfonyl" radicals having one to six carbon atoms. Even more preferred are lower haloalkylsulfonyl radicals having one to three carbon atoms. Examples of such lower haloalkylsulfonyl radicals include trifluoromethylsulfonyl. The term "arylalkylsulfonyl" embraces aryl radicals as defined above, attached to an alkylsulfonyl radical. Examples of such radicals include benzylsulfonyl and phenylethylsulfonyl. The term "heterocyclosulfonyl" embraces heterocyclo radicals as defined above, attached to a sulfonyl radical. More preferred heterocyclosulfonyl radicals contain 5–7 membered heterocyclo radicals containing one or two heteroatoms. Examples of such radicals include tetrahydropyrrolylsulfonyl morpholinylsulfonyl and azepinylsulfonyl.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$). The term "alkylaminosulfonyl" includes "N-alkylaminosulfonyl" and "N,N-dialkylaminosulfonyl" where sulfamyl radicals are substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl. The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylsulfonyl radicals having one to three carbon atoms. Examples of such lower N-alkyl-N-arylaminosulfonyl radicals include N-methyl-N-phenylaminosulfonyl and N-ethyl-N-phenylaminosulfonyl. Examples of such N-aryl-aminosulfonyl radicals include N-phenylaminosulfonyl. The term "arylalkylaminosulfonyl" embraces aralkyl radicals as described above, attached to an aminosulfonyl radical. More preferred are lower arylalkylaminosulfonyl radicals having one to three carbon atoms. The term "heterocyclylaminosulfonyl" embraces heterocyclyl radicals as described above, attached to an aminosulfonyl radical.

The terms "carboxy" or "carboxyl", whether used alone or with other terms, such as "carboxyalkyl", denotes —CO$_2$H. The term "carboxyalkyl" embraces radicals having a carboxy radical as defined above, attached to an alkyl radical.

The term "carbonyl", whether used alone or with other terms, such as "alkylcarbonyl", denotes —(C═O)—.

The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl.

The term "aroyl" embraces aryl radicals with a carbonyl radical as defined above. Examples of aroyl include benzoyl, naphthoyl, and the like and the aryl in said aroyl may be additionally substituted.

The term "alkylcarbonyl" embraces radicals having a carbonyl radical substituted with an alkyl radical. More preferred alkylcarbonyl radicals are "lower alkylcarbonyl" radicals having one to six carbon atoms. Even more preferred are lower alkylcarbonyl radicals having one to three carbon atoms. Examples of such radicals include methylcarbonyl and ethylcarbonyl. The term "haloalkylcarbonyl" embraces radicals having a carbonyl radical substituted with an haloalkyl radical. More preferred haloalkylcarbonyl radicals are "lower haloalkylcarbonyl" radicals having one to six carbon atoms. Even more preferred are lower haloalkylcarbonyl radicals having one to three carbon atoms. Examples of such radicals include trifluoromethylcarbonyl.

The term "arylcarbonyl" embraces radicals having a carbonyl radical substituted with an aryl radical. More preferred arylcarbonyl radicals include phenylcarbonyl. The term "heteroarylcarbonyl" embraces radicals having a carbonyl radical substituted with a heteroaryl radical. Even more preferred are 5- or 6-membered heteroarylcarbonyl radicals. The term "arylalkylcarbonyl" embraces radicals having a carbonyl radical substituted with an arylalkyl radical. More preferred radicals are phenyl-$C_1$–$C_3$-alkylcarbonyl, including benzylcarbonyl. The term "heteroarylalkylcarbonyl" embraces radicals having a carbonyl radical substituted with a heteroarylalkyl radical. Even more preferred are lower heteroarylalkylcarbonyl radicals having 5–6-membered heteroaryl radicals attached to alkyl portions having one to three carbon atoms.

The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. Even more preferred are lower alkoxycarbonyl radicals having alkoxy portions of one to three carbon atoms.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$. The terms "N-alkylaminocarbonyl" and "N,N-dialkylaminocarbonyl" denote aminocarbonyl radicals which have been substituted with one alkyl radical and with two alkyl radicals, respectively. More preferred are "lower alkylaminocarbonyl" having lower alkyl radicals as described above attached to an aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical. The term "N-cycloalkylaminocarbonyl" denoted aminocarbonyl radicals which have been substituted with at least one cycloalkyl radical. More preferred are "lower cycloalkylaminocarbonyl" having lower cycloalkyl radicals of three to seven carbon atoms, attached to an aminocarbonyl radical.

The term "aminoalkyl" embraces alkyl radicals substituted with amino radicals. The term "alkylaminoalkyl" embraces aminoalkyl radicals having the nitrogen atom substituted with an alkyl radical. Even more preferred are lower alkylaminoalkyl radicals having one to three carbon atoms. The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy. The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, halkoalkyl and haloalkoxy. The term "arylalkynyl" embraces aryl-substituted alkynyl radicals. Preferable arylalkynyl radicals are "lower arylalkynyl" radicals having aryl radicals attached to alkynyl radicals having two to six carbon atoms. Examples of such radicals include phenylethynyl. The aryl in said aralkyl, arylalkenyl and arylalkynyl may be additionally substituted with halo, alkyl, alkoxy, halkoalkyl and haloalkoxy.

The terms benzyl and phenylmethyl are interchangeable.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3$—S—). The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms. The term "arylsulfinyl" embraces radicals containing an aryl radical, attached to a divalent —S(=O)— atom. Even more preferred are optionally substituted phenylsulfinyl radicals. The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms.

The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "heteroarylamino" denotes amino groups which have been substituted with one or two heteroaryl radicals, such as N-thienylamino. The "heteroarylamino" radicals may be further substituted on the heteroaryl ring portion of the radical. The term "aralkylamino" denotes amino groups which have been substituted with one or two aralkyl radicals. More preferred are phenyl-$C_1$–$C_3$-alkylamino radicals, such as N-benzylamino. The "aralkylamino" radicals may be further substituted on the aryl ring portion of the radical. The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio. The term "aralkylthio" embraces aralkyl radicals as described above, attached to a divalent sulfur atom. More preferred are phenyl-$C_1$–$C_3$-alkylthio radicals. An example of "aralkylthio" is benzylthio. The term "aralkylsulfonyl" embraces aralkyl radicals as described above, attached to a divalent sulfonyl radical. More preferred are phenyl-$C_1$–$C_3$-alkylsulfonyl radicals.

The term "aryloxy" embraces optionally substituted aryl radicals, as defined above, attached to an oxygen atom. Examples of such radicals include phenoxy. The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

Additional Synthetic Procedures

The intermediates, thiophene compounds and functionalized thiophene compounds discussed above can be synthesized, for example, according to the procedures set forth below, or by appropriate modification of these general synthetic procedures. The substituents of the compounds shown in the following procedures have the same definition as the substituents at the corresponding position in the compounds of Formulae I–VI, except where further noted.

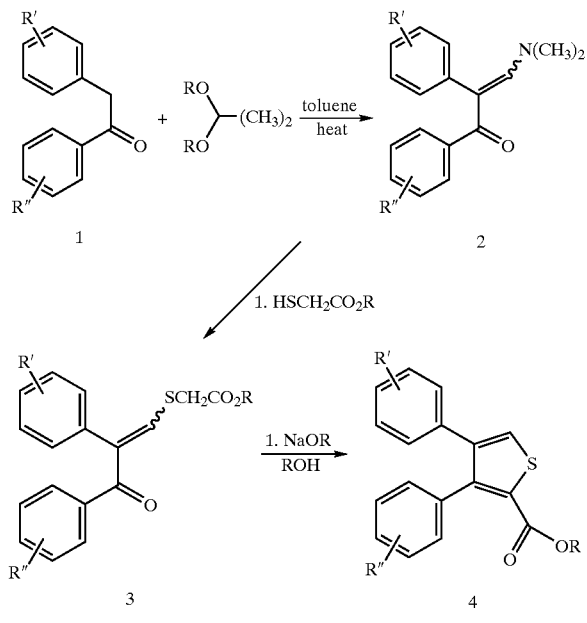

One approach for the preparation of optionally substituted 3,4-diarylthiophenes 4 is outlined in Scheme I. Diphenyl ethanones 1 (wherein each phenyl moiety may be substituted with one or more functional groups) and an acetal (shown here as an acetal of dimethyl-formamide) are refluxed together in a suitable solvent such as toluene. Upon removal of the solvent and excess acetal, the enamine 2 is obtained. The enamine 2 is refluxed in a suitable solvent (such as 1,2 dichloroethane) with an ester of thioacetic acid (or alternatively thioacetic acid or an amide of thioacetic acid) which affords the mixture of Michael addition products 3. The solvent is removed at reduced pressure. The residue is then taken up in an alcoholic solvent and a ring cyclizing reagent, such as the corresponding sodium alkoxide, is added. Upon mixing at room temperature the desired tri-substituted thiophenes 4 were obtained after purification.

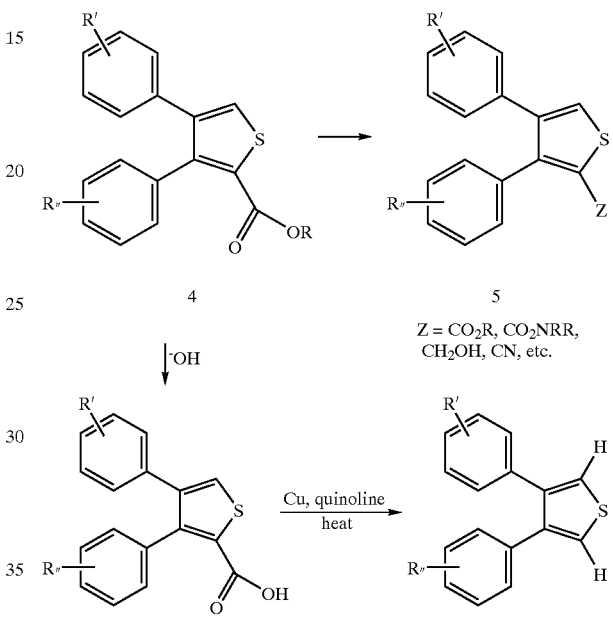

As outlined in Scheme II, standard organic laboratory procedures can be employed to manipulate the ester group of thiophene 4 into a number of different functional groups such as alcohols, alkyls, alkenes, alkynes, amides, cyanos, etc. Alternatively, the ester group can be saponified and the resulting carboxylic acid 6 removed through a copper-mediated decarboxylation affording the 3,4-substituted diphenylthiophene 7.

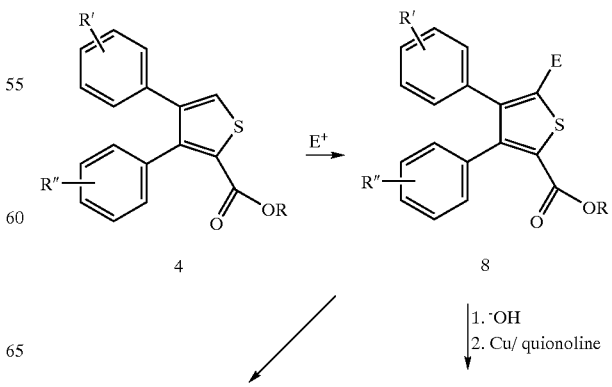

-continued

9

E = Cl Br, I, NO$_2$
Z = CO$_2$R, CO$_2$NRR,
CH$_2$OH, CN, etc.

10

E = Cl, Br, I, NO$_2$

Alternatively, as outlined in Scheme III the remaining thiophene-ring hydrogen of thiophene 4 can be converted to a halogen or nitro group to form thiophene 8. The ester group of thiophene 8 then can be manipulated as described above to provide a variety of functional groups, such as for thiophenes 9 and 10.

Working Example

The following example contains a detailed description of the methods of preparation of compounds of Formulae I–VI. The detailed description falls within the scope, and serves to exemplify, the previously-described processes which form part of the invention. The detailed description is presented for illustrative purposes only and is not intended as a restriction on the scope of the invention. All parts are by weight and temperatures are in Degrees centigrade unless otherwise indicated. All compounds showed NMR spectra consistent with their assigned structures.

The following abbreviations are used:

HCl—hydrochloric acid
DMSO—dimethylsulfoxide
DMSOd$_6$—deuterated dimethylsulfoxide
CDCl$_3$—deuterated chloroform
MgSO$_4$—magnesium sulfate
NaHCO$_3$—sodium bicarbonate
KHSO$_4$—potassium hydrogen sulfate
DMF—dimethylformamide
NaOH—sodium hydroxide
BOC—tert butyloxycarbonyl
CD$_3$OD—deuterated methanol
EtOH—ethanol
LiOH—lithium hydroxide
CH$_2$Cl$_2$—methylene chloride
h—hour
hr—hour
min—minutes
THF—tetrahydrofuran
TLC—thin layer chromatography
Et$_3$N—triethylamine
DBU—1,8-diazabicyclo[5.4.0]undec-7-ene
DMAP—4-dimethylaminopyridine

EXAMPLE 1

Methyl 3-[3-Fluoro-4-(sulfonamido)phenyl]-4-phenyl-2-thiophenecarboxylate

Step 1: Preparation of 3-Fluoro-4-(methylthio)-benzaldehyde

The 3,4-diflourobenzaldehyde (52.1 g, 0.36 mol) was dissolved in acetonitrile (500 mL). Sodium thiomethoxide (25.6 g, 0.36 mol) was added in four equal portions at 15 minute intervals. The slightly exothermic reaction was stirred at room temperature for 4 hours. The reaction mixture was poured into ethyl acetate (500 mL) and extracted with saturated sodium bicarbonate (2×200 mL) followed by saturated ammounium chloride (2×100 mL). The solution was dried over sodium sulfate and solvent removed at reduced pressure. The 3-flouro-4-(methylthio)-benzaldehyde (38.5 g, 0.22 mol) was isolated by vacuum distillation (135–145° C. at 25 mm Hg) as clear liquid. (61% yield) ESHRMS m/z 171.0302 (calcd for M+H, 171.0280).

Step 2: Preparation of 3-fluoro-4-(methylthio)-a-[(trimethysilyl)oxy]-benzeneacetonitrile The 3-flouro-4-methylthiobenzaldehyde (33.0 g, 194.0 mmol), trimethylsilyl cyanide (19.8 g, 200 mmol) were mixed together in dichloromethane (350 mL) and zinc iodide (35 mg) was addded. The solution was heated to 35° C. The bath was removed and the solution stirred for 1 hour during which an exotherm was noted. After cooling to room temperature the solvent was removed at reduced pressure to afford the 3-fluoro-4-(methylthio)-a-[(trimethylsilyl)oxy] benzene-acetonitrile (51.6 g, 192 mmol) as a yellow oil. (98% yield): $^1$H NMR (CHCl$_3$/300 MHz) 7.24–7.29 (m, 3H), 5.48 (s, 1H), 2.51 (s, 3H), 0.27 (s, 9H). ESHRMS m/z 261.0769 (calcd for M+H, 261.0749).

Step 3: Preparation of 1-[3-fluoro-4-(methylthio)-phenyl]-2-phenylethanone

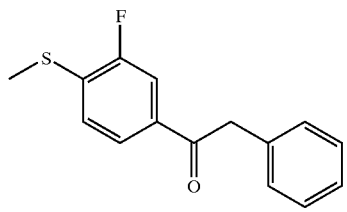

The 3-fluoro-4-(methylthio)-a-[(trimethylsilyl)-oxy]-benzeneacetonitrile (40.1 g, 149 mmol) was cooled to −78° C. in tetrahydrofuran(400 mL). Lithium hexamethydisilazide (175 mL of 1.0 M in Hexanes, 175 mmol) was added dropwise over 1 hour. The solution was stirred for 1 additional hour at −78° C. Benzylbromide (24.5 g 149 mmol) was added as a solution in tetrahydrofuran (100 mL) over 25 minutes. The solution was kept at −78° C. for 1 hour, warmed to room temperature, and kept at room temperature for six hours. The solution was poured into ethyl acetate (300 mL). Aqueous 1 N hydrochloric acid (200 mL) was added and the solution stirred for 48 hours at room temperature. The layers were separated and the organic layer collected. The organic layer was mixed with aqueous 15% sodium hydroxide and stirred for 30 minutes. The organic layer was collected washed with saturated ammounium chloride(200 mL) and solution was dried over sodium sulfate and solvent removed at reduced pressure to afford a yellow oil. The product was isolated by preparative silica chromatography followed by crystallization from 2% ethyl acetate and hexanes (400 mL). 1-[3-fluoro-4-(methylthio)phenyl]-2-phenylethanone (21.5 grams, 82.0 mmol) was obtained as white crystals. (55% yield): Mp 77.1–77.2° C. $^1$H NMR (CDCl$_3$/300 MHz) 7.77, (dd, 1H, J=8.0, 1.8 Hz), 7.64 (dd, 1H, J=10.7, 1.8 Hz), 7.20–7.40 (m, 6H), 4.22 (s, 3H), 2.51 (s, 1H).

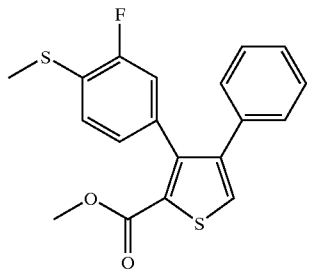

The 1-[3-fluoro-4-(methylthio)phenyl]-2-phenylethanone (21.9 g, 81.5 mmol) and dimethylacetal of dimethylformamide (41.3 g, 347 mmol) were refluxed in toluene (200 mL) for 16 hours. The yellow solution was cooled to room temperature and solvent removed at reduced pressure. The resulting yellow oil was dissolved in 50% ethyl acetate/50% hexanes (200 mL) and vacuum filtered through silica gel. The silica was washed with 50% ethyl acetate/50% hexanes (150 mL). The filtrates were combined and solvent removed at reduced pressure to afford 25.19 g the enamine (shown below) as a yellow oil.

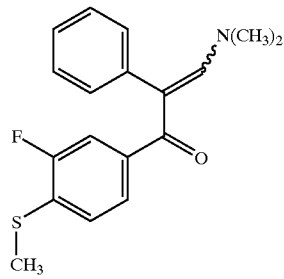

The enamine (25.09 g, 79.3 mmol) and methyl thioglycolate (35.5 g, 326 mmol) were refluxed in 1,2-dichloroethane (250 mL) for 16 hours. The solvent was removed at reduced pressure and the resulting oil taken up in methanol (300 mL). 25% sodium methoxide in methanol (75.0 mL, 326 mmol) was added and the reaction stirred. After 20 minutes of mixing a precipitate formed and the mixing ceased. The solution was kept at room temperature for 6 hours and the crystals collected. Methyl 3-[3-fluoro-4-(methylthio)phenyl]-4-phenyl-2-thiophenecarboxylate (18.3 grams, 51.7 mmol) was isolated as white crystals. 200 mg of the lot was recrystalized from ethyl acetate and hexanes for analytical data and the remainder used without further purification.(64% Yield): Mp 140.6–141.0° C. $^1$H NMR (CDCl$_3$/300 MHz) 7.52 (s, 1H), 7.52 (s, 1H), 7.21–7.80 (m, 3H), 7.17 (t, 1H, J=8.0 Hz),7.06–7.12 (m, 2H), 6.86–6.97 (m, 2H), 3.81 (s, 3H), 2.50 (s, 3H). ESHRMS m/z 359.0598 (calcd for M+H$^+$, 359.0576).

Step 5: Preparation of methyl 3-[3-fluoro-4-(methylsulfinyl)phenyl]-4-phenyl-2-thiophenecarboxylate.

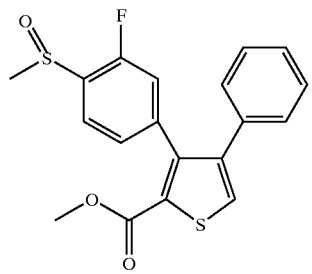

The methyl 3-[3-fluoro-4-(methylthio)phenyl]-4-phenyl-2-thiophenecarboxylate (5.00 g, 13.9 mmol) was dissolved in dichloromethane (100 mL) and methanol (30 mL). Magnesium monoperoxyphathalate hexahydrate (MMPP)(3.78 g of 80%, 7.6 mmol) was added in five equal portions at one minute intervals. The resulting heterogeneous solution was stirred for 1 hour. Additional MMPP (600 mg, 1.6 mmol) was added and the solution stirred for 15 min. The reaction was complete and solution extracted with saturated sodium bicarbonate (2×100 mL). The organic layer was dried over sodium sulfate and solvent removed at reduced pressure. Methyl 3-[3-fluoro-4-(methylsulfinyl)phenyl]-4-phenyl-2-thiophenecarboxylate was isolated by crystallization from dichloromethane and hexanes. (81% yield): Mp 164.0–164.1° C. $^1$H NMR (CDCl$_3$/300 MHz) 7.75 (t, 1H, J=7.7 Hz), 7.53 (s, 1H), 7.15–7.26 (m, 3H), 6.94–7.40 (m, 3H), 3.90 (s, 3H), 2.85 (s, 3H). ESHRMS m/z 375.0536 (calcd for M+H, 375.0525).

Step 6: Preparation of methyl 3-[4-[[(acetyloxy)-methyl]thio]-3-fluorophenyl]-4-phenyl-2-thiophenecarboxylate

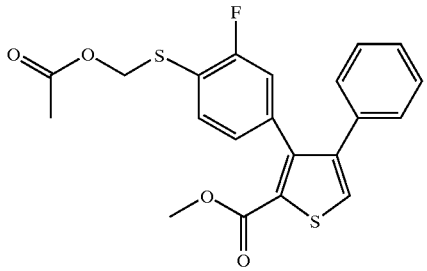

The methyl 3-[3-fluoro-4-(methylsulfinyl)phenyl]-4-phenyl-2-thiophenecarboxylate (4.13 g, 11.04 mmol) was dissolved in acetic anhydride (45.0 mL). Powdered sodium acetate (4.0 g, 48.7 mmol) was added and the solution was refluxed for 8 hours. The solution was poured into a 500 mL round bottom flask and solvent removed at reduced pressure. The residue was taken up in ethyl acetate (200 ml) and dichloromethane (20 mL). The solution was extracted with saturated sodium bicarbonate (3×100 mL) followed by saturated ammonium chloride (2×100 mL). The solvent was removed at reduce pressure and residue taken up in ether, dried over sodium sulfate and solvent removed at reduced pressure. Methyl 3-[4-[[(acetyloxy)methyl]thio]-3-fluorophenyl]-4-phenyl-2-thiophenecarboxylate (2.9 g, 6.90 mmol) was isolated by crystallization from diethyl ether and hexanes as white crystals. (62% yield). Mp 102.9–103.7° C. $^1$H NMR (CDCl$_3$/300 MHz) 7.53 (s, 1H), 7.43 (t, 1H, J=7.8 Hz), 7.22–7.28 (m, 3H), 7.04–7.08 (m, 2H), 6.92–6.98 (m, 2H), 5.42 (s, 2H), 3.81 (s, 3H), 2.11 (s, 3H). ESHRMS m/z 434.0898 (calcd for M+NH$_4^+$, 434.0896)

Step 7: Preparation of methyl 3-[4-[[(acetyloxy)methyl]-sulfonyl]3-fluorophenyl]-4-phenyl-2-thiophenecarboxylate

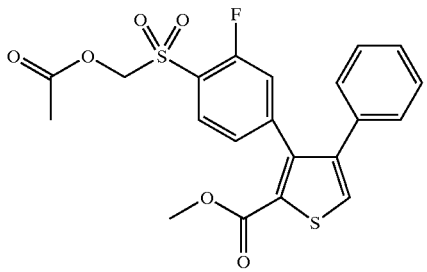

The methyl 3-[4-[[(acetyloxy)methyl]thio]-3-fluorophenyl]-4-phenyl-2-thiophenecarboxylate (3.56 g, 8.55 mmol), MMPP (5.80 g of 80%, 9.45 mmol) were mixed in methanol (30 mL) and dichloromethane (100 mL). The solution was mixed at room temperature for 16 h and additional MMPP (2.00 g) was added. The solution was heated to reflux for 8 hours. The solution was poured into ethyl acetate (200 mL) and extracted with saturated aqueous sodium bicarbonate (2×100 mL) followed by brine (100 mL). The organic layer was collected and solvent removed at reduced pressure. The resulting white semi-solid was triturated with ethyl acetate and hexanes. Methyl 3-[4-[[(acetyloxy)methyl]-sulfonyl]3-fluorophenyl]-4-phenyl-2-thiophene-carboxylate (3.15 g, 7.03 mmol) was isolated as an off white solid. (82% yield). Mp 164.7–164.8° C. $^1$H NMR (CDCl$_3$/300 MHz) 7.82 (t, 1H, J=7.5 Hz), 7.56 (s, 1H), 7.22–7.30 (m, 2H), 7.13 (d, 2H, J=9.2 Hz), 7.00–7.67 (m, 2H), 5.35 (s, 2H), 3.82 (s, 3H), 2.09 (s, 3H). ESHRMS m/z 466.0796 (calcd for M+NH$_4^+$, 466.0794).

Step 8: Preparation of 2-methyl 3-(3-fluoro-4-sulfinophenyl)-4-phenyl-2-thiophenecarboxylate

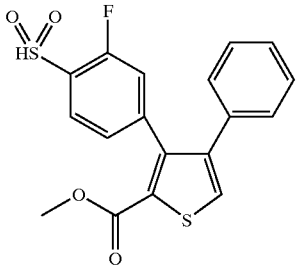

The methyl 3-[4-[[(acetyloxy)methyl]sulfonyl]3-fluorophenyl]-4-phenyl-2-thiophenecarboxylate (2.75 g, 6.13 mmol) was dissolved in tetrahydrofuran (100 mL) and stirred at room temperature. 25% Sodium methoxide in methanol (3.0 mL) was added and the solution stirred for 5 min. The resulting slurry was poured into ethyl acetate (200 mL) and aqueous 1N hydrochloric acid (100 mL) was added. The solution was stirred and the layers allowed to separate. The organic layer was collected and the aqueous layer back extracted with ethyl acetate (100 mL). The organic layers were combined, extracted with brine, dried over sodium sulfate, and solvent removed at reduced pressure. The 2-methyl 3-(3-fluoro-4-sulfinophenyl)-4-phenyl-2-thiophenecarboxylate (1.87 g, 4.59 mmol) was isolated as a white solid.(77% yield). Mp 132.6–133.1° C. $^1$H NMR (CDCl$_3$/300 MHz) 7.74–7.80 (1H, m), 7.55 (s, 1H), 6.80–7.28 (m, 6H), 3.74 (s, 3H). ESHRMS m/z 394.0586 (calcd for M+NH$_4^+$, 394.0583).

Step 9: Preparation of methyl 3-[3-fluoro-4-(sulfonamido)phenyl]-4-phenyl-2-thiophenecarboxylate

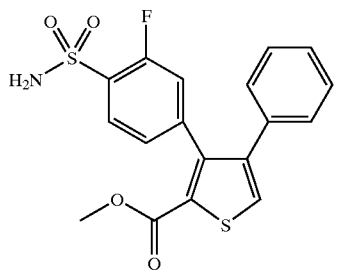

The 2-methyl 3-(3-fluoro-4-sulfinophenyl)-4-phenyl-2-thiophenecarboxylate (1.51 g, 4.01 mmol) was dissolved in methanol (25 mL). Water (10 mL) was added and the solution became slightly clouldy. Sodium acetate (2.62 g, 32.0 mmol) and hydroxyamine-O-sulfonic acid (1.80 g, 16.6 mmol) were mixed toeghter at room temperature for 4 Hours. The solution was poured into ethyl acetate (100 mL) and extracted with 1N aqueous hydrochloric acid (2×50 mL), water (2×50 mL), saturated sodium bicarbonate (2×50 mL) and brine (50 mL). The solution was dried over anhydrous sodium sulfate and solvent removed at reduced pressure. The methyl 3-[3-fluoro-4-(sulfonamido)phenyl]-4-phenyl-2-thiophene-carboxylate (1.04 g, 2.65 mmol) was isolated as a white solid by crystallizations from ethyl acetate and hexanes. (66% yield). Mp 168.3–168.4° C. $^1$H NMR (CDCl$_3$/300 MHz) 7.78 (t, 1H, J=7.6 Hz), 7.51 (s, 1H), 7.20–7.61 (m, 3H), 6.80–7.10 (m, 4H), 5.01 (bs, 2H), 3.77 (s, 3H). ESHRMS m/z 409.0684 (calcd for M+NH$_4^+$, 409.0692).

As various changes could be made in the above processes and apparatus without departing from the scope of the invention, it is intended that all matter contained in the above description be interpreted as illustrative and not in a limiting sense. All documents mentioned in this application are expressly incorporated by reference as if fully set forth at length.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A process for the preparation of a compound of Formula V:

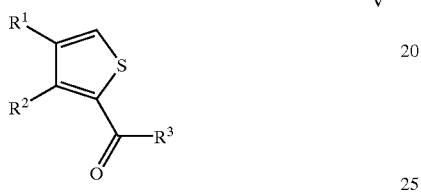

the process comprising reacting a compound of Formula IV:

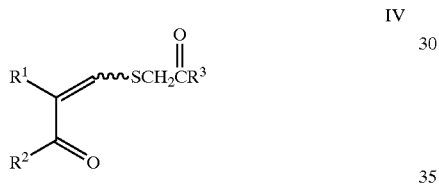

with a ring cyclizing reagent to form a compound of Formula V, wherein:
$R^1$ is optionally substituted carbocyclyl;
$R^2$ is optionally substituted carbocyclyl;
$R^3$ is selected from —$OR^6$ and —$NR^7R^8$; and
$R^6$, $R^7$ and $R^8$ are independently selected from hydrogen, hydrocarbyl and heterosubstituted hydrocarbyl.

2. The process of claim 1 wherein the ring cyclizing reagent is an alkoxide.

3. The process of claim 1 wherein the ring cyclizing reagent is an alkali metal alkoxide.

4. The process of claim 1 wherein the ring cyclizing reagent is sodium methoxide.

5. The process of claim 1 comprising reacting a compound of Formula IV with an alkali metal alkoxide to form a compound of Formula V, wherein:
$R^1$ is selected from optionally substituted cycloalkyl, cycloalkenyl, and aryl;
$R^2$ is selected from optionally substituted cycloalkyl, cycloalkenyl, and aryl;
$R^3$ is selected from —$OR^6$ and —$NR^7R^8$; and
$R^6$, $R^7$ and $R^8$ are independently selected from hydrogen and optionally substituted alkyl, alkenyl, alkynyl, cycloalkyl, cycloalkenyl, aryl, heterocyclyl, arylalkyl and heterocyclylalkyl, wherein said alkyl may have one or more carbon atoms that are optionally replaced with oxygen atoms.

6. The process of claim 5 wherein:
$R^1$ is optionally substituted aryl;
$R^2$ is optionally substituted aryl;
$R^3$ is selected from —$OR^6$ and —$NR^7R^8$; and
$R^6$, $R^7$ and $R^8$ are independently selected from hydrogen and optionally substituted alkyl, alkenyl, alkynyl, cycloalkyl, cycloalkenyl, aryl, heterocyclyl, arylalkyl and heterocyclylalkyl, wherein said alkyl may have one or more carbon atoms that are optionally replaced with oxygen atoms.

7. The process of claim 5 wherein:
$R^1$ is optionally substituted phenyl;
$R^2$ is optionally substituted phenyl;
$R^3$ is selected from —$OR^6$ and —$NR^7R^8$; and
$R^6$, $R^7$ and $R^8$ are independently selected from hydrogen and optionally substituted lower alkyl, lower alkenyl, 3–6 member ring cycloalkyl, 3–6 member ring cycloalkenyl, phenyl, (phenyl)-lower alkyl and (5- or 6-member heteroaryl)-lower alkyl, wherein said alkyl may have one or more carbon atoms that are optionally replaced with oxygen atoms.

8. The process of claim 5 wherein:
one of $R^1$ and $R^2$ is phenyl optionally substituted with one, two or three radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, alkylsulfonyl, aminosulfonyl, halo, alkoxy and alkylthio;
the other of $R^1$ and $R^2$ is phenyl optionally substituted with one, two or three radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, alkylsulfonyl, aminosulfonyl, halo, alkoxy and alkylthio;
$R^3$ is selected from —$OR^6$ and —$NR^7R^8$; and
$R^6$, $R^7$ and $R^8$ are independently selected from hydrogen and optionally substituted alkyl, alkenyl, alkynyl, 3–6 member ring cycloalkyl, 3–6 member ring cycloalkenyl, 5 or 6-member ring aryl, 5- or 6-member ring heteroaryl, phenylalkyl and (5- or 6-member heteroaryl)alkyl.

9. The process of claim 5 wherein:
one of $R^1$ and $R^2$ is phenyl optionally substituted with one, two or three radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, lower alkylsulfonyl, aminosulfonyl, halo, lower alkoxy and lower alkylthio;
the other of $R^1$ and $R^2$ is phenyl optionally substituted with one, two or three radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, lower alkylsulfonyl, aminosulfonyl, halo, lower alkoxy and lower alkylthio;
$R^3$ is selected from —$OR^6$ and —$NR^7R^8$; and
$R^6$, $R^7$ and $R^8$ are independently selected from hydrogen and optionally substituted lower alkyl, lower alkenyl, 3–6 member ring cycloalkyl, phenyl, 5- or 6-member ring heteroaryl, (phenyl)-lower alkyl, and (5- or 6-member ring heteroaryl)-lower alkyl.

10. The process of claim 5 wherein:
one of $R^1$ and $R^2$ is phenyl optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, $C_{1-2}$-alkylsulfonyl, aminosulfonyl, halo, $C_{1-2}$-alkoxy and $C_{1-2}$-alkylthio;

the other of $R^1$ and $R^2$ is phenyl optionally substituted with one, two or three radicals selected from $C_{1-2}$-alkyl, $C_{1-2}$-haloalkyl, cyano, carboxyl, $C_{1-2}$-alkoxycarbonyl, hydroxyl, $C_{1-2}$-hydroxyalkyl, $C_{1-2}$-haloalkoxy, amino, $C_{1-2}$-alkylamino, phenylamino, nitro, $C_{1-2}$-alkoxy-$C_{1-2}$-alkyl, $C_{1-2}$-alkylsulfinyl, $C_{1-2}$-alkylsulfonyl, aminosulfonyl, halo, $C_{1-2}$-alkoxy and $C_{1-2}$-alkylthio;

$R^3$ is selected from —$OR^6$ and —$NR^7R^8$;

$R^4$ and $R^5$ are independently selected from optionally substituted $C_{1-4}$-alkyl; and $R^6$, $R^7$ and $R^8$ are independently selected from hydrogen and optionally substituted $C_{1-3}$-alkyl, $C_{1-3}$-alkenyl, 3–6 member ring cycloalkyl, phenyl, 5- or 6-member ring heteroaryl, (phenyl)$C_{1-3}$-alkyl, (5- or 6-member ring heteroaryl)$C_{1-3}$-alkyl.

11. The process of claim 4 wherein:

one of $R^1$ and $R^2$ is phenyl optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, methylsulfonyl, aminosulfonyl, fluoro, chloro, bromo, methoxy and methylthio;

the other of $R^1$ and $R^2$ is phenyl optionally substituted with one, two or three radicals selected from methyl, difluoromethyl, trifluoromethyl, cyano, carboxyl, methoxycarbonyl, hydroxyl, hydroxymethyl, trifluoromethoxy, amino, methylamino, phenylamino, nitro, methoxymethyl, methylsulfinyl, methylsulfonyl, aminosulfonyl, fluoro, chloro, bromo, methoxy and methylthio;

$R^3$ is selected from —$OR^6$ and —$NR^7R^8$; and $R^6$, $R^7$ and $R^8$ are independently selected from hydrogen and optionally substituted methyl, ethyl, propyl, t-butyl, ethenyl, propenyl, propynyl, cyclopropyl, cyclobutyl, cyclopentyl, cyclohexyl, cyclobutenyl, cyclopentenyl, cyclohexenyl, phenyl, pyridinyl, pyrimidinyl, and benzyl.

12. The process of claim 5 wherein:

one of $R^1$ and $R^2$ is phenyl optionally substituted with one, two or three radicals selected from halo, cyano, $C_{1-2}$-alkyl, $C_{1-2}$-haloalkyl, $C_{1-2}$-alkoxy, $C_{1-2}$-haloalkoxy, $C_{1-2}$-alkylsulfonyl, aminosulfonyl;

the other of $R^1$ and $R^2$ is phenyl optionally substituted with one, two or three radicals selected from halo, cyano, $C_{1-2}$-alkyl, $C_{1-2}$-haloalkyl, $C_{1-2}$-alkoxy, $C_{1-2}$-haloalkoxy, $C_{1-2}$-alkylsulfonyl, aminosulfonyl;

$R^3$ is selected from —$OR^6$ and —$NR^7R^8$; and $R^6$, $R^7$ and $R^8$ are independently selected from hydrogen and optionally substituted $C_{1-3}$-alkyl, $C_{1-3}$-alkenyl, 3–6 member ring cycloalkyl, phenyl, 5- or 6-member ring heteroaryl, (phenyl)$C_{1-3}$-alkyl, and (5- or 6-member ring heteroaryl)$C_{1-3}$-alkyl.

13. The process of claim 5 wherein:

$R^1$ is phenyl optionally substituted with one, two or three radicals selected from methyl, difluoromethyl, trifluoromethyl, trifluoromethoxy, cyano, methylsulfonyl, aminosulfonyl, fluoro, chloro, bromo, and methoxy;

$R^2$ is phenyl optionally substituted with one, two or three radicals selected from methyl, difluoromethyl, trifluoromethyl, trifluoromethoxy, cyano, methylsulfonyl, aminosulfonyl, fluoro, chloro, bromo, and methoxy;

$R^3$ is selected from —$OR^6$ and —$NR^7R^8$; and $R^6$, $R^7$ and $R^8$ are independently selected from hydrogen and optionally substituted methyl, ethyl, propyl and benzyl.

14. The process of claim 1 wherein the compound of Formula IV is prepared by reacting a compound of Formula III:

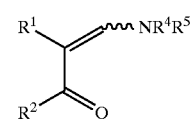

III with a compound selected from the group consisting of thioacetic acid, esters of thioacetic acid and amides of thioacetic acid, wherein:

$R^1$, $R^2$ and $R^3$ are as defined in claim 1; and $R^4$ and $R^5$ are independently selected from hydrogen and optionally substituted alkyl.

15. The process of claim 1 comprising:

reacting a compound of Formula III:

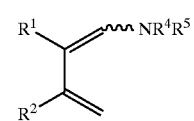

III with a compound selected from the group consisting of thioacetic acid, esters of thioacetic acid and amides of thioacetic acid to form a compound of Formula IV:

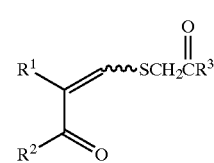

IV and reacting said compound of Formula IV with a ring cyclizing reagent to form a compound of Formula V; wherein said compound of Formula IV is isolated in substantially purified form before it is reacted with the ring cyclizing reagent; and wherein:

$R^1$ is selected from optionally substituted carbocyclyl;

$R^2$ is selected from optionally substituted carbocyclyl;

$R^3$ is selected from —$OR^6$ and —$NR^7R^8$;

$R^4$ and $R^5$ are independently selected from hydrogen and optionally substituted alkyl; and $R^6$, $R^7$ and $R^8$ are independently selected from hydrogen, hydrocarbyl and heterosubstituted hydrocarbyl.

16. The process of claim 1 wherein the compound of Formula IV is reacted with the ring cyclizing reagent in a suitable solvent.

17. The process of claim 1 wherein the solvent is selected from the group consisting of alcohols and ethereal solvents.

18. The process of claim 1 wherein the solvent is an alcohol.

19. The process of claim 1 wherein the solvent is methanol.

20. The process of claim 1 wherein the compound of Formula IV is reacted with an alkoxide base in an alcohol solvent.

21. The process of claim 20 wherein the alkoxide is an alkali metal alkoxide.

22. The process of claim 15 wherein the compound of Formula III is reacted with the compound selected from the group consisting of thioacetic acid, esters of thioacetic acid and amides of thioacetic acid in a suitable solvent under reflux conditions.

23. The process of claim 15 wherein the compound of Formula III is reacted with the compound selected from the group consisting of thioacetic, esters of thioacetic acid and amides of thioacetic acid in 1,2-dichloroethane under reflux conditions.

* * * * *